United States Patent [19]

Nielsen et al.

[11] Patent Number: 5,773,571
[45] Date of Patent: Jun. 30, 1998

[54] PEPTIDE NUCLEIC ACIDS

[76] Inventors: Peter E. Nielsen, Hjortevanget 509, DK 2980 Kokkedal; Ole Buchardt, Sondergardsvej 73, DK 3500 Vaerlose; Michael Egholm, Johnstrup Alle 3, DK 1923 Frederiksberg; Rolf H. Berg, Strandvaenget 6, DK 2960 Rungsted Kyst, all of Denmark

[21] Appl. No.: 595,387

[22] Filed: Feb. 1, 1996

Related U.S. Application Data

[60] Division of Ser. No. 54,363, Apr. 26, 1993, Pat. No. 5,539,082, which is a continuation-in-part of Ser. No. 108,591, filed as PCT/EP92/01219, May 22, 1992, published as WO92/20702, Nov. 26, 1992.

[51] Int. Cl.[6] .............................. C12Q 1/68; C07K 5/00
[52] U.S. Cl. ............................ 530/300; 435/6; 436/501; 514/2; 514/44; 536/23.1; 536/24.1; 536/24.3; 536/24.31; 536/24.32; 536/24.33; 536/25.3; 935/77; 935/78
[58] Field of Search ................................... 435/5, 6, 810, 435/501; 514/2, 44; 530/300, 350; 536/23.1, 24.1, 24.3–24.33, 25.3; 935/77, 78

[56] References Cited

U.S. PATENT DOCUMENTS

| 5,134,066 | 7/1992 | Rogers et al. | 435/91 |
|---|---|---|---|
| 5,142,047 | 8/1992 | Summerton et al. | 544/118 |

FOREIGN PATENT DOCUMENTS

| 8605518 | 9/1986 | WIPO . |
|---|---|---|
| WO 92/20703 | 11/1992 | WIPO . |
| WO 93/12129 | 6/1993 | WIPO . |

OTHER PUBLICATIONS

Almarrson, et al., "Molecular Mechanics Calculations of the Structures of Polyamide Nucleic Acid DNA Duplexes and Triple Helical Hybrids", *PNAS USA*, 1993, 90, 7518–7522.

Buttrey, et al., "Synthetic Analogues of Polynucleotides", *Tetrahedron*, 1975, 31, 73–75.

Depto et al., "Regulated Expression of the Human Cytomegalovirus pp65 Gene: Octamer Sequence in the Promoter Is Required for Activation by Viral Gene Products," *J. Virol.*, 1989, 63, 1232–1238.

Doel, et al., "The Synthesis of Peptides Containing Purine and Pyrimidine Derivatives of DL–Alanine", *Tetrahedron*, 1974, 30, 2755–2759.

Dubochet, et al., "A New Preparation Method for Dark–Field Electron Microscopy of Biomacromolecules,"*J. Ultrastruct. Res.*, 1971, 35, 147–167.

Egholm, "Peptide Nucleic Acids (PNA). Oligonucleotide Analogues with an Achiral Peptide Backbone", *J. Am. Chem. Soc.*, 1992, 114, 1895–1897.

Egholm, et al., "Peptide Nucleic Acids (PNA): A Novel Approach to Sequence–Selective Recognition of Double–Stranded DNA", pp. 325–328, in *Innovation and Perspectives in Solid Phase Synthesis, Collected Papers*, 1992.

Froehler et al., "Oligodeoxynucleotides Containing C–5 Propyne Analogs of 2'–Deoxyuridine and 2'–Deoxycytidine," *Tetrahedron Letters*, 1992, 33, 5307–5310.

Gerwirtz, "Therapeutic Applications of Antisense DNA in the Treatment of Human Leukemia", 178–187 in *Antisense Strategies*, Vol. 660, published 1992, by The New York Academy of Sciences.

Hahn et. al., "Molecular cloning and characterization of the HTLV–III virus associated with AIDS,"*Nature*, 1984, 312, 166–169.

Hanvey, et al., "Antisense and Antigene Properties of Peptide Nucleic Acids", *Science*, 1992, 258, 1481–1485.

Hyrup, et al., "Modification of the Binding Affinity of Peptide Nucleic Acids (PNA). PNA with Extended Backbones Consisting of 2–Aminoethyl–B–alanine or 3–Aminopropylglycine Units",*J. Chem. Soc., Chem. Commun.*, 1993, 6, 518–519.

Lal et al., "Diphenylphosphoryl Azide, A Novel Reagent for the Stereospecific Synthesis of Azides from Alcohols[1]", *Tetrahedron Letters*, 1977, 23, 1977–1980.

Lu, et al., "Synthesis of Polyesters Containing Nucleic And Base Derivatives as Pending Side Chains",*J. Poly. Sci., Part A: Polychem.*, 1986, 24, 525–536.

McCurdy et al., "Deoxyoligonucleotides with Inverted Polarity: Synthesis and Use in Triple–Helix Formation," *Nucleosides and Nucleotides*, 1991, 10 (1–3), 287–290.

Meier, et al., "Peptide Nucleic Acids(PNAs)–Unusual Properties of Nonionic Oligonucleotide Analogues", *Angew. Chem. Int. Ed. Eng.*, 1992, 31(8l), 1008–1010.

Nielsen, et al., "Sequence–Selective Recognition of DNA by Strand Displacement with a Thymine–Substituted Polyamide", *Science*, (1991), 254, 1497–1500.

Sagi et. al., "Base–Modified Oligodeoxynucleotides. I. Effect of 5–Alkyl, 5–(1–Alkenyl) and 5–(l–Alkynyl) Substitution of the Pyrimidines on Duplex Stability and Hydrophobicity," *Tetrahedron Letters*, 1993, 34, 2191–2194.

Spalholtz et al., "Bovive papillomavirus Transcriptional Regulation: Localization of the E2–Responsive Elements of the Long Control Region," *J. Virol.*, 1987,61, 2128–2137.

Stenberg et al., "Promoter–Specific trans Activation and Repression by Human Cytomegalovirus Immediate–Early Proteins Involves Common and Unique Protein Domains," *J. Virol.*, 1990, 64, 1556–1565.

(List continued on next page.)

*Primary Examiner*—Ardin H. Marschel
*Attorney, Agent, or Firm*—Woodcock Washburn Kurtz Mackiewicz & Norris LLP

[57] ABSTRACT

A novel class of compounds, known as peptide nucleic acids, bind complementary ssDNA and RNA strands more strongly than a corresponding DNA. The peptide nucleic acids generally comprise ligands such as naturally occurring DNA bases attached to a peptide backbone through a suitable linker.

11 Claims, No Drawings

OTHER PUBLICATIONS

Takemoto, et al., "Synthetic Nucleic Acid Analogs, Preparation and Interaction", *Adv. Poly. Sci.,* (1981), 1–51.

Tibanyenda, et al., "The effect of single base–pair mismatches on the duplex stability of d(T–A–T–T–A–A–T–A–T–C–A–A–G–T–T–G) . d(C–A–A–C–T–T–G–A–T–A–T–T–A–A–T–A)," *Eur. J. Biochem.,* 1984, 139, 19–27.

Vasseur, et al., "Oligonucleosides: Synthesis of a Novel Methylhydroxylamine–Linked Nucleoside Dimer and Its Incorporation into Antisense Sequences," *J. Am. Chem. Soc.,* 1992, 114, 4006–4007.

Vickers, et al., "Inhibition of HIV–LTR gene expression by oligonucleotides targeted to the TAR element," *Nucleic Acids Research,* 1991, 19, 3359–3368.

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 11 amino acids
( B ) TYPE: amino acid
( C ) STRANDEDNESS: single
( D ) TOPOLOGY: unknown ( i i ) MOLECULE TYPE: peptide ( i x ) FEATURE:
( A ) NAME/KEY: Modified-site
( B ) LOCATION: 1
( D ) OTHER INFORMATION: /label=MODIFIED-SITE
/ note= "Thymine heterocycle is attached to
N-acetyl(2- aminoethyl)glycine through the
N-acetyl group at position 1 of the heterocycle."

( i x ) FEATURE:
( A ) NAME/KEY: Modified-site
( B ) LOCATION: 2
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 3
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 4
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 5
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 6
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 7
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 8
( D ) OTHER INFORMATION: /label=Modified-site
/ note= "Thymine heterocycle is attached to
N-acetyl(2- aminoethyl)glycine through the N-acetyl group at position 1 of the heterocycle."

( i x ) FEATURE:
  ( A ) NAME/KEY: Modified-site
  ( B ) LOCATION: 9
  ( D ) OTHER INFORMATION: /label=Modified-site
   / note= "Thymine heterocycle is attached to
   N-acetyl(2- aminoethyl)glycine through the N-acetyl
   group at position 1 of the heterocycle."

( i x ) FEATURE:
  ( A ) NAME/KEY: Modified-site
  ( B ) LOCATION: 10
  ( D ) OTHER INFORMATION: /label=Modified-site
   / note= "Thymine heterocycle is attached to
   N-acetyl(2- aminoethyl)glycine through the N-acetyl
   group at position 1 of the heterocycle."

( x i ) SEQUENCE DESCRIPTION: SEQ ID NO:1:

Xaa Xaa Xaa Xaa Xaa Xaa Xaa Xaa Xaa Xaa Lys
1       5         10

( 2 ) INFORMATION FOR SEQ ID NO:2:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: unknown ( i i ) MOLECULE TYPE: peptide ( i x ) FEATURE:
  ( A ) NAME/KEY: Modified-site
  ( B ) LOCATION: 1
  ( D ) OTHER INFORMATION: /label=Modified-site
   / note= "Thymine heterocycle is attached to
   N-acetyl(2- aminoethyl)glycine through the N-acetyl
   group at position 1 of the heterocycle."

( i x ) FEATURE:
  ( A ) NAME/KEY: Modified-site
  ( B ) LOCATION: 2
  ( D ) OTHER INFORMATION: /label=Modified-site
   / note= "Thymine heterocycle is attached to
   N-acetyl(2- aminoethyl)glycine through the N-acetyl
   group at position 1 of the heterocycle."

( i x ) FEATURE:
  ( A ) NAME/KEY: Modified-site
  ( B ) LOCATION: 3
  ( D ) OTHER INFORMATION: /label=Modified-site
   / note= "Thymine heterocycle is attached to
   N-acetyl(2- aminoethyl)glycine through the N-acetyl
   group at position 1 of the heterocycle."

( i x ) FEATURE:
  ( A ) NAME/KEY: Modified-site
  ( B ) LOCATION: 4
  ( D ) OTHER INFORMATION: /label=Modified-site
   / note= "Thymine heterocycle is attached to
   N-acetyl(2- aminoethyl)glycine through the N-acetyl
   group at position 1 of the heterocycle."

( i x ) FEATURE:
  ( A ) NAME/KEY: Modified-site
  ( B ) LOCATION: 5
  ( D ) OTHER INFORMATION: /label=Modified-site
   / note= "Cytosine heterocycle is attached to
   N-acetyl(2- aminoethyl)glycine through the N-acetyl
   group at postion 1 of the heterocycle."

( i x ) FEATURE:
  ( A ) NAME/KEY: Modified-site
  ( B ) LOCATION: 6
  ( D ) OTHER INFORMATION: /label=Modified-site
   / note= "Thymine heterocycle is attached to
   N-acetyl(2- aminoethyl)glycine through the N-acetyl group at position 1 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( x i ) SEQUENCE DESCRIPTION: SEQ ID NO:2:

Xaa Xaa Xaa Xaa Xaa Xaa Xaa Xaa Xaa Xaa Lys
1                     5                              10

( 2 ) INFORMATION FOR SEQ ID NO:3:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: unknown ( i i ) MOLECULE TYPE: peptide ( i x ) FEATURE:
    ( A ) NAME/KEY: Modified-site
    ( B ) LOCATION: 1
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 2
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 3
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 4
    ( D ) OTHER INFORMATION: /label=Modified-site
        / note= "Thymine heterocycle is attached to
        N-acetyl(2- aminoethyl)glycine through the N-acetyl -continued group at position 1 of the heterocycle."

( i x ) FEATURE:
    ( A ) NAME/KEY: Modified-site
    ( B ) LOCATION: 5
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 6
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( x i ) SEQUENCE DESCRIPTION: SEQ ID NO:3:

```
Xaa  Xaa  Xaa  Xaa  Xaa  Xaa  Xaa  Xaa  Xaa  Xaa  Lys
1                  5                          10
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 2
        ( D ) OTHER INFORMATION: /label=Modified-site
            / note= "Thymine heterocycle is attached to
            N-acetyl(2- aminoethyl)glycine through the N-acetyl group at position 1 of the heterocycle."

( i x ) FEATURE:
    ( A ) NAME/KEY: Modified-site
    ( B ) LOCATION: 3
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 4
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 5
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 6
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( x i ) SEQUENCE DESCRIPTION: SEQ ID NO:4:

```
Xaa  Xaa  Xaa  Xaa  Xaa  Xaa  Xaa  Xaa  Xaa  Xaa  Lys
1                     5                          10
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 2
        ( D ) OTHER INFORMATION: /label=Modified-site
            / note= "Guanine heterocycle is attached to
            N-acetyl(2- aminoethyl)glycine through the N-acetyl
            group at position 9 of the heterocycle."

( i x ) FEATURE:
        ( A ) NAME/KEY: Modified-site
        ( B ) LOCATION: 3
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 4
        ( D ) OTHER INFORMATION: /label=Modified-site
            / note= "Adenine heterocycle is attached to
            N-acetyl(2- aminoethyl)glycine through the N-acetyl
            group at position 9 of the heterocycle."

( i x ) FEATURE:
        ( A ) NAME/KEY: Modified-site
        ( B ) LOCATION: 5
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 6
        ( D ) OTHER INFORMATION: /label=Modified-site
            / note= "Guanine heterocycle is attached to
            N-acetyl(2- aminoethyl)glycine through the N-acetyl
            group at position 9 of the heterocycle."

( i x ) FEATURE:
        ( A ) NAME/KEY: Modified-site
        ( B ) LOCATION: 7
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 8
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 9
        ( D ) OTHER INFORMATION: /label=Modified-site
            / note= "Adenine heterocycle is attached to
            N-acetyl(2- aminoethyl)glycine through the N-acetyl
            group at position 9 of the heterocycle."

( i x ) FEATURE:
        ( A ) NAME/KEY: Modified-site
        ( B ) LOCATION: 10
        ( D ) OTHER INFORMATION: /label=Modified-site
            / note= "Cytosine heterocycle is attached to
            N-acetyl(2- aminoethyl)glycine through the N-acetyl group at position 1 of the heterocycle."

(ix) FEATURE:
    (A) NAME/KEY: Modified-site
    (B) LOCATION: 11
    (D) OTHER INFORMATION: /label=Modified-site
    / note= "Adenine heterocycle is attached to
    N-acetyl(2- aminoethyl)glycine through the N-acetyl
    group at position 9 of the heterocycle."

(ix) FEATURE:
    (A) NAME/KEY: Modified-site
    (B) LOCATION: 12
    (D) OTHER INFORMATION: /label=Modified-site
    / note= "Adenine heterocycle is attached to
    N-acetyl(2- aminoethyl)glycine through the N-acetyl
    group at position 9 of the heterocycle."

(ix) FEATURE:
    (A) NAME/KEY: Modified-site
    (B) LOCATION: 13
    (D) OTHER INFORMATION: /label=Modified-site
    / note= "Cytosine heterocycle is attached to
    N-acetyl(2- aminoethyl)glycine through the N-acetyl
    group at position 1 of the heterocycle."

(ix) FEATURE:
    (A) NAME/KEY: Modified-site
    (B) LOCATION: 14
    (D) OTHER INFORMATION: /label=Modified-site
    / note= "Thymine heterocycle is attached to
    N-acetyl(2- aminoethyl)glycine through the N-acetyl
    group at position 1 of the heterocycle."

(ix) FEATURE:
    (A) NAME/KEY: Modified-site
    (B) LOCATION: 15
    (D) OTHER INFORMATION: /label=Modified-site
    / note= "Adenine heterocycle is attached to
    N-acetyl(2- aminoethyl)glycine through the N-acetyl
    group at position 9 of the heterocycle."

(xi) SEQUENCE DESCRIPTION: SEQ ID NO:5:

Xaa Xaa Xaa Xaa Xaa Xaa Xaa Xaa Xaa Xaa Xaa Xaa Xaa Xaa Xaa
1               5                     10                 15

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label=Modified-site
        / note= "Cytosine heterocycle is attached to
        N-acetyl(2- aminoethyl)glycine through the N-acetyl
        group at position 1 of the heterocycle."

(ix) FEATURE:
        (A) NAME/KEY: Modified-site
        (B) LOCATION: 2
        (D) OTHER INFORMATION: /label=Modified-site
        / note= "Cytosine heterocycle is attached to
        N-acetyl(2- aminoethyl)glycine through the N-acetyl
        group at position 1 of the heterocycle."

(ix) FEATURE:
        (A) NAME/KEY: Modified-site
        (B) LOCATION: 3
        (D) OTHER INFORMATION: /label=Modified-site
        / note= "Thymine heterocycle is attached to
        N-acetyl(2- aminoethyl)glycine through the N-acetyl group at position 1 of the heterocycle."

( i x ) FEATURE:
        ( A ) NAME/KEY: Modified-site
        ( B ) LOCATION: 4
        ( D ) OTHER INFORMATION: /label=Modified-site
                / note= "Thymine heterocycle is attached to
                N-acetyl(2- aminoethyl)glycine through the N-acetyl
                group at position 1 of the heterocycle."

( i x ) FEATURE:
        ( A ) NAME/KEY: Modified-site
        ( B ) LOCATION: 5
        ( D ) OTHER INFORMATION: /label=Modified-site
                / note= "Cytosine heterocycle is attached to
                N-acetyl(2- aminoethyl)glycine through the N-acetyl
                group at position 1 of the heterocycle."

( i x ) FEATURE:
        ( A ) NAME/KEY: Modified-site
        ( B ) LOCATION: 6
        ( D ) OTHER INFORMATION: /label=Modified-site
                / note= "Cytosine heterocycle is attached to
                N-acetyl(2- aminoethyl)glycine through the N-acetyl
                group at position 1 of the heterocycle."

( i x ) FEATURE:
        ( A ) NAME/KEY: Modified-site
        ( B ) LOCATION: 7
        ( D ) OTHER INFORMATION: /label=Modified-site
                / note= "Cytosine heterocycle is attached to
                N-acetyl(2- aminoethyl)glycine through the N-acetyl
                group at position 1 of the heterocycle."

( i x ) FEATURE:
        ( A ) NAME/KEY: Modified-site
        ( B ) LOCATION: 8
        ( D ) OTHER INFORMATION: /label=Modified-site
                / note= "Thymine heterocycle is attached to
                N-acetyl(2- aminoethyl)glycine through the N-acetyl
                group at position 1 of the heterocycle."

( i x ) FEATURE:
        ( A ) NAME/KEY: Modified-site
        ( B ) LOCATION: 9
        ( D ) OTHER INFORMATION: /label=Modified-site
                / note= "Thymine heterocycle is attached to
                N-acetyl(2- aminoethyl)glycine through the N-acetyl
                group at position 1 of the heterocycle."

( x i ) SEQUENCE DESCRIPTION: SEQ ID NO:6:

Xaa  Xaa  Xaa  Xaa  Xaa  Xaa  Xaa  Xaa  Xaa
1                      5

( 2 ) INFORMATION FOR SEQ ID NO:7:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: unknown ( i i ) MOLECULE TYPE: peptide ( i x ) FEATURE:
            ( A ) NAME/KEY: Modified-site
            ( B ) LOCATION: 1
            ( D ) OTHER INFORMATION: /label=Modified-site
                    / note= "Thymine heterocycle is attached to
                    N-acetyl(2- aminoethyl)glycine through the N-acetyl
                    group at position 1 of the heterocycle."

( i x ) FEATURE:
            ( A ) NAME/KEY: Modified-site
            ( B ) LOCATION: 2
            ( D ) OTHER INFORMATION: /label=Modified-site
                    / note= "Thymine heterocycle is attached to
                    N-acetyl(2- aminoethyl)glycine through the N-acetyl group at position 1 of the heterocycle."

( i x ) FEATURE:
 ( A ) NAME/KEY: Modified-site
 ( B ) LOCATION: 3
 ( D ) OTHER INFORMATION: /label=Modified-site
  / note= "Cytosine heterocycle is attached to
  N-acetyl(2- aminoethyl)glycine through the N-acetyl
  group at position 1 of the heterocycle."

( i x ) FEATURE:
 ( A ) NAME/KEY: Modified-site
 ( B ) LOCATION: 4
 ( D ) OTHER INFORMATION: /label=Modified-site
  / note= "Cytosine heterocycle is attached to
  N-acetyl(2- aminoethyl)glycine through the N-acetyl
  group at position 1 of the heterocycle."

( i x ) FEATURE:
 ( A ) NAME/KEY: Modified-site
 ( B ) LOCATION: 5
 ( D ) OTHER INFORMATION: /label=Modified-site
  / note= "Cytosine heterocycle is attached to
  N-acetyl(2- aminoethyl)glycine through the N-acetyl
  group at position 1 of the heterocycle."

( i x ) FEATURE:
 ( A ) NAME/KEY: Modified-site
 ( B ) LOCATION: 6
 ( D ) OTHER INFORMATION: /label=Modified-site
  / note= "Thymine heterocycle is attached to
  N-acetyl(2- aminoethyl)glycine through the N-acetyl
  group at position 1 of the heterocycle."

( i x ) FEATURE:
 ( A ) NAME/KEY: Modified-site
 ( B ) LOCATION: 7
 ( D ) OTHER INFORMATION: /label=Modified-site
  / note= "Thymine heterocycle is attached to
  N-acetyl(2- aminoethyl)glycine through the N-acetyl
  group at position 1 of the heterocycle."

( i x ) FEATURE:
 ( A ) NAME/KEY: Modified-site
 ( B ) LOCATION: 8
 ( D ) OTHER INFORMATION: /label=Modified-site
  / note= "Cytosine heterocycle is attached to
  N-acetyl(2- aminoethyl)glycine through the N-acetyl
  group at position 1 of the heterocycle."

( i x ) FEATURE:
 ( A ) NAME/KEY: Modified-site
 ( B ) LOCATION: 9
 ( D ) OTHER INFORMATION: /label=Modified-site
  / note= "Cytosine heterocycle is attached to
  N-acetyl(2- aminoethyl)glycine through the N-acetyl
  group at position 1 of the heterocycle."

( x i ) SEQUENCE DESCRIPTION: SEQ ID NO:7:

Xaa  Xaa  Xaa  Xaa  Xaa  Xaa  Xaa  Xaa  Xaa
1                     5

( 2 ) INFORMATION FOR SEQ ID NO:8:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: unknown ( i i ) MOLECULE TYPE: peptide ( i x ) FEATURE:
  ( A ) NAME/KEY: Modified-site
  ( B ) LOCATION: 1
  ( D ) OTHER INFORMATION: /label=Modified-site
   / note= "Thymine heterocycle is attached to
   N-acetyl(2- aminoethyl)glycine through the N-acetyl group at position 1 of the heterocycle."

( i x ) FEATURE:
    ( A ) NAME/KEY: Modified-site
    ( B ) LOCATION: 2
    ( D ) OTHER INFORMATION: /label=Modified-site
        / note= "Adenine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 3
    ( D ) OTHER INFORMATION: /label=Modified-site
        / note= "Guanine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 4
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 5
    ( D ) OTHER INFORMATION: /label=Modified-site
        / note= "Thymine heterocycle is attached to
        N-acety(2- aminoethyl)glycine through the N-acetyl
        group at position 1 of the heterocycle."

( i x ) FEATURE:
    ( A ) NAME/KEY: Modified-site
    ( B ) LOCATION: 6
    ( D ) OTHER INFORMATION: /label=Modified-site
        / note= "Adenine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 11
    ( D ) OTHER INFORMATION: /label=Modified-site
        / note= "Thymine heterocycle is attached to
        N-acetyl(2- aminoethyl)glycine through the N-acetyl group at position 1 of the heterocycle."

(ix) FEATURE:
    (A) NAME/KEY: Modified-site
    (B) LOCATION: 12
    (D) OTHER INFORMATION: /label=Modified-site
    / note= "Adenine heterocycle is attached to
    N-acetyl(2- aminoethyl)glycine through the N-acetyl
    group at position 9 of the heterocycle."

(ix) FEATURE:
    (A) NAME/KEY: Modified-site
    (B) LOCATION: 13
    (D) OTHER INFORMATION: /label=Modified-site
    / note= "Thymine heterocycle is attached to
    N-acetyl(2- aminoethyl)glycine through the N-acetyl
    group at position 1 of the heterocycle."

(ix) FEATURE:
    (A) NAME/KEY: Modified-site
    (B) LOCATION: 14
    (D) OTHER INFORMATION: /label=Modified-site
    / note= "Cytosine heterocycle is attached to
    N-acetyl(2- aminoethyl)glycine through the N-acetyl
    group at position 1 of the heterocycle."

(ix) FEATURE:
    (A) NAME/KEY: Modified-site
    (B) LOCATION: 15
    (D) OTHER INFORMATION: /label=Modified-site
    / note= "Thymine heterocycle is attached to
    N-acetyl(2- aminoethyl)glycine through the N-acetyl
    group at position 1 of the heterocycle."

(xi) SEQUENCE DESCRIPTION: SEQ ID NO:8:

Xaa Xaa Xaa Xaa Xaa Xaa Xaa Xaa Xaa Xaa Xaa Xaa Xaa Xaa Xaa
1                5                        10                    15

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
        (A) NAME/KEY: Modified-site
        (B) LOCATION: 2
        (D) OTHER INFORMATION: /label=Modified-site
        / note= "Guanine heterocycle is attached to
        N-acetyl(2- aminoethyl)glycine through the N-acetyl
        group at position 9 of the heterocycle."

(ix) FEATURE:
        (A) NAME/KEY: Modified-site
        (B) LOCATION: 3
        (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
        (A) NAME/KEY: Modified-site
        (B) LOCATION: 4
        (D) OTHER INFORMATION: /label=Modified-site
        / note= "Adenine heterocycle is attached to
        N-acetyl(2- aminoethyl)glycine through the N-acetyl group at position 9 of the heterocycle."

( i x ) FEATURE:
    ( A ) NAME/KEY: Modified-site
    ( B ) LOCATION: 5
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 6
    ( D ) OTHER INFORMATION: /label=Modified-site
        / note= "Guanine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Adenine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 10
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 11
    ( D ) OTHER INFORMATION: /label=Modified-site
        / note= "Adenine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 12
    ( D ) OTHER INFORMATION: /label=Modified-site
        / note= "Adenine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 13
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 14
    ( D ) OTHER INFORMATION: /label=Modified-site
        / note= "Thymine heterocycle is attached to
        N-acetyl(2- aminoethyl)glycine through the N-acetyl group at position 1 of the heterocycle."

(ix) FEATURE:
  (A) NAME/KEY: Modified-site
  (B) LOCATION: 15
  (D) OTHER INFORMATION: /label=Modified-site
    / note= "Adenine heterocycle is attached to
    N-acetyl(2- aminoethyl)glycine through the N-acetyl
    group at position 9 of the heterocycle."

(xi) SEQUENCE DESCRIPTION: SEQ ID NO:9:

Xaa Xaa Xaa Xaa Xaa Xaa Xaa Xaa Xaa Xaa Xaa Xaa Xaa Xaa Xaa
1               5                   10                  15

(2) INFORMATION FOR SEQ ID NO:10:

(i) SEQUENCE CHARACTERISTICS:
    (A) LENGTH: 9 amino acids
    (B) TYPE: amino acid
    (C) STRANDEDNESS: single
    (D) TOPOLOGY: unknown (ii) MOLECULE TYPE: peptide (ix) FEATURE:
    (A) NAME/KEY: Modified-site
    (B) LOCATION: 1
    (D) OTHER INFORMATION: /label=Modified-site
      / note= "Guanine heterocycle is attached to
      N-acetyl(2- aminoethyl)glycine through the N-acetyl
      group at position 9 of the heterocycle."

(ix) FEATURE:
    (A) NAME/KEY: Modified-site
    (B) LOCATION: 2
    (D) OTHER INFORMATION: /label=Modified-site
      / note= "Cytosine heterocycle is attached to
      N-acetyl(2- aminoethyl)glycine through the N-acetyl
      group at position 1 of the heterocycle."

(ix) FEATURE:
    (A) NAME/KEY: Modified-site
    (B) LOCATION: 3
    (D) OTHER INFORMATION: /label=Modified-site
      / note= "Adenine heterocycle is attached to
      N-acetyl(2- aminoethyl)glycine through the N-acetyl
      group at position 9 of the heterocycle."

(ix) FEATURE:
    (A) NAME/KEY: Modified-site
    (B) LOCATION: 4
    (D) OTHER INFORMATION: /label=Modified-site
      / note= "Cytosine heterocycle is attached to
      N-acetyl(2- aminoethyl)glycine through the N-acetyl
      group at position 1 of the heterocycle."

(ix) FEATURE:
    (A) NAME/KEY: Modified-site
    (B) LOCATION: 5
    (D) OTHER INFORMATION: /label=Modified-site
      / note= "Adenine heterocycle is attached to
      N-acetyl(2- aminoethyl)glycine through the N-acetyl
      group at position 9 of the heterocycle."

(ix) FEATURE:
    (A) NAME/KEY: Modified-site
    (B) LOCATION: 6
    (D) OTHER INFORMATION: /label=Modified-site
      / note= "Guanine heterocycle is attached to
      N-acetyl(2- aminoethyl)glycine through the N-acetyl
      group at position 9 of the heterocycle."

(ix) FEATURE:
    (A) NAME/KEY: Modified-site
    (B) LOCATION: 7
    (D) OTHER INFORMATION: /label=Modified-site
      / note= "Cytosine heterocycle is attached to
      N-acetyl(2- aminoethyl)glycine through the N-acetyl group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( x i ) SEQUENCE DESCRIPTION: SEQ ID NO:10:

Xaa Xaa Xaa Xaa Xaa Xaa Xaa Xaa Lys
1                            5

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 2
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 3
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 4
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 5
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 6
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 7
        ( D ) OTHER INFORMATION: /label=Modified-site
            / note= "Thymine heterocycle is attached to
            N-acetyl(2- aminoethyl)glycine through the N-acetyl group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( x i ) SEQUENCE DESCRIPTION: SEQ ID NO:11:

```
Xaa  Xaa  Xaa  Xaa  Xaa  Xaa  Xaa  Xaa  Xaa
1                        5
```

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 2
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 3
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 4
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 5
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 6
        ( D ) OTHER INFORMATION: /label=Modified-site
            / note= "Thymine heterocycle is attached to
            N-acetyl(2- aminoethyl)glycine through the N-acetyl group at position 1 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 11
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 12
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 13
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 14
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 15
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 16
    ( D ) OTHER INFORMATION: /label=Modified-site
        / note= "Cytosine heterocycle is attached to
        N-acetyl(2- aminoethyl)glycine through the N-acetyl group at position 1 of the heterocycle."

( x i ) SEQUENCE DESCRIPTION: SEQ ID NO:12:

Xaa Xaa Xaa Xaa Xaa Xaa Xaa Xaa Xaa Xaa Xaa Xaa Xaa Xaa Xaa Xaa
1               5                       10                      15

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 2
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 3
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 4
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 5
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 6
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 7
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 8
        ( D ) OTHER INFORMATION: /label=Modified-site
            / note= "Thymine heterocycle is attached to
            N-acetyl(2- aminoethyl)glycine through the N-acetyl -continued group at position 1 of the heterocycle."

(ix) FEATURE:
    (A) NAME/KEY: Modified-site
    (B) LOCATION: 9
    (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
    (A) NAME/KEY: Modified-site
    (B) LOCATION: 10
    (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
    (A) NAME/KEY: Modified-site
    (B) LOCATION: 11
    (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
    (A) NAME/KEY: Modified-site
    (B) LOCATION: 12
    (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
    (A) NAME/KEY: Modified-site
    (B) LOCATION: 13
    (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
    (A) NAME/KEY: Modified-site
    (B) LOCATION: 14
    (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
    (A) NAME/KEY: Modified-site
    (B) LOCATION: 15
    (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
    (A) NAME/KEY: Modified-site
    (B) LOCATION: 16
    (D) OTHER INFORMATION: /label=Modified-site
        / note= "Thymine heterocycle is attached to
        N-acetyl(2- aminoethyl)glycine through the N-acetyl
        group at position 1 of the heterocycle."

(xi) SEQUENCE DESCRIPTION: SEQ ID NO:13:

```
Xaa Xaa Xaa Xaa Xaa Xaa Xaa Xaa Xaa Xaa Xaa Xaa Xaa Xaa Xaa Xaa
 1               5                  10                 15
```

(2) INFORMATION FOR SEQ ID NO:14:

(i) SEQUENCE CHARACTERISTICS:
        (A) LENGTH: 10 amino acids
        (B) TYPE: amino acid
        (C) STRANDEDNESS: single
        (D) TOPOLOGY: unknown ( i i ) MOLECULE TYPE: peptide ( i x ) FEATURE:
    ( A ) NAME/KEY: Modified-site
    ( B ) LOCATION: 1
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 2
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 3
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 4
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 5
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 6
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Cytosine heterocycle is attached to
        N-acetyl(2- aminoethyl)glycine through the N-acetyl group at position 1 of the heterocycle."

(xi) SEQUENCE DESCRIPTION: SEQ ID NO:14:

Xaa Xaa Xaa Xaa Xaa Xaa Xaa Xaa Xaa Xaa
1               5                           10

(2) INFORMATION FOR SEQ ID NO:15:

(i) SEQUENCE CHARACTERISTICS:
      (A) LENGTH: 10 amino acids
      (B) TYPE: amino acid
      (C) STRANDEDNESS: single
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
      (A) NAME/KEY: Modified-site
      (B) LOCATION: 2
      (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
      (A) NAME/KEY: Modified-site
      (B) LOCATION: 3
      (D) OTHER INFORMATION: /label=Modified-site
        / note= "Cytosine heterocycle is attached to
        N-acetyl(2- aminoethyl)glycine through the N-acetyl
        group at position 1 of the heterocycle."

(ix) FEATURE:
      (A) NAME/KEY: Modified-site
      (B) LOCATION: 4
      (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
      (A) NAME/KEY: Modified-site
      (B) LOCATION: 5
      (D) OTHER INFORMATION: /label=Modified-site
        / note= "Cytosine heterocycle is attached to
        N-acetyl(2- aminoethyl)glycine through the N-acetyl
        group at position 1 of the heterocycle."

(ix) FEATURE:
      (A) NAME/KEY: Modified-site
      (B) LOCATION: 6
      (D) OTHER INFORMATION: /label=Modified-site
        / note= "Thymine heterocycle is attached to
        N-acetyl(2- aminoethyl)glycine through the N-acetyl
        group at position 1 of the heterocycle."

(ix) FEATURE:
      (A) NAME/KEY: Modified-site
      (B) LOCATION: 7
      (D) OTHER INFORMATION: /label=Modified-site
        / note= "Cytosine heterocycle is attached to
        N-acetyl(2- aminoethyl)glycine through the N-acetyl
        group at position 1 of the heterocycle."

(ix) FEATURE:
      (A) NAME/KEY: Modified-site
      (B) LOCATION: 8
      (D) OTHER INFORMATION: /label=Modified-site
        / note= "Thymine heterocycle is attached to
        N-acetyl(2- aminoethyl)glycine through the N-acetyl group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( x i ) SEQUENCE DESCRIPTION: SEQ ID NO:15:

Xaa Xaa Xaa Xaa Xaa Xaa Xaa Xaa Xaa Xaa
1                   5                               1 0

( 2 ) INFORMATION FOR SEQ ID NO:16:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
    ( A ) NAME/KEY: Modified-site
    ( B ) LOCATION: 1
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 2
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 3
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 4
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 5
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 6
    ( D ) OTHER INFORMATION: /label=Modified-site
        / note= "Cytosine heterocycle is attached to
        N-acetyl(2- aminoethyl)glycine through the N-acetyl group at position 1 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 11
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 12
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 13
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 14
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 15
    ( D ) OTHER INFORMATION: /label=Modified-site
        / note= "Thymine heterocycle is attached to
        N-acety(2- aminoethyl)glycine through the N-acetyl
        group at position 1 of the heterocycle."

( x i ) SEQUENCE DESCRIPTION: SEQ ID NO:16:

```
Xaa  Xaa  Xaa  Xaa  Xaa  Xaa  Xaa  Xaa  Xaa  Xaa  Xaa  Xaa  Xaa  Xaa  Xaa
1                   5                        10                       15
```

( 2 ) INFORMATION FOR SEQ ID NO:17:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 2
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 3
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 4
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 5
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 6
        ( D ) OTHER INFORMATION: /label=Modified-site
            / note= "Adenine heterocycle is attached to
            N-acetyl(2- aminoethyl)glycine through the N-acetyl
            group at position 9 of the heterocycle."

( i x ) FEATURE:
        ( A ) NAME/KEY: Modified-site
        ( B ) LOCATION: 7
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 8
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 9
        ( D ) OTHER INFORMATION: /label=Modified-site
            / note= "Adenine heterocycle is attached to
            N-acetyl(2- aminoethyl)glycine through the N-acetyl group at position 9 of the heterocycle."

( i x ) FEATURE:
    ( A ) NAME/KEY: Modified-site
    ( B ) LOCATION: 10
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 11
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 12
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 13
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 14
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 15
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 16
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 17
    ( D ) OTHER INFORMATION: /label=Modified-site
        / note= "Thymine heterocycle is attached to
        N-acetyl(2- aminoethyl)glycine through the N-acetyl
        group at position 1 of thr heterocycle."

( i x ) FEATURE:
    ( A ) NAME/KEY: Modified-site
    ( B ) LOCATION: 18
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 19
    ( D ) OTHER INFORMATION: /label=Modified-site
        / note= "Thymine heterocycle is attached to
        N-acetyl(2- aminoethyl)glycine through the N-acetyl group at position 1 of the heterocycle."

( i x ) FEATURE:
    ( A ) NAME/KEY: Modified-site
    ( B ) LOCATION: 20
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( x i ) SEQUENCE DESCRIPTION: SEQ ID NO:17:

Xaa Xaa Xaa Xaa Xaa Xaa Xaa Xaa Xaa Xaa Xaa Xaa Xaa Xaa Xaa Xaa
1             5                         10                       15

Xaa Xaa Xaa Xaa Lys Lys Lys Lys Lys Lys Lys Lys Lys
        20                       25

( 2 ) INFORMATION FOR SEQ ID NO:18:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Cytosine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 2
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 3
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 4
        ( D ) OTHER INFORMATION: /label=Modified-site
            / note= "Adenine heterocycle is attached to
            N-acetyl(2- aminoethyl)glycine through the N-acetyl
            group at position 9 of the heterocycle."

( i x ) FEATURE:
        ( A ) NAME/KEY: Modified-site
        ( B ) LOCATION: 5
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 6
        ( D ) OTHER INFORMATION: /label=Modified-site
            / note= "Adenine heterocycle is attached to
            N-acetyl(2- aminoethyl)glycine through the N-acetyl
            group at position 9 of the heterocycle."

( i x ) FEATURE:
        ( A ) NAME/KEY: Modified-site
        ( B ) LOCATION: 7

-continued (D) OTHER INFORMATION: /label=Modified-site
/ note= "Thymine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 8
(D) OTHER INFORMATION: /label=Modified-site
/ note= "Thymine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 9
(D) OTHER INFORMATION: /label=Modified-site
/ note= "Cytosine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 10
(D) OTHER INFORMATION: /label=Modified-site
/ note= "Cytosine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 11
(D) OTHER INFORMATION: /label=Modified-site
/ note= "Guanine heterocycle is attached to
N-acetyl(2- aminoethyl)glycine through the N-acetyl
group at position 9 of the heterocycle."

(ix) FEATURE:
(A) NAME/KEY: Modified-site
(B) LOCATION: 12
(D) OTHER INFORMATION: /label=Modified-site
/ note= "Thymine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 13
(D) OTHER INFORMATION: /label=Modified-site
/ note= "Cytosine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 14
(D) OTHER INFORMATION: /label=Modified-site
/ note= "Adenine heterocycle is attached to
N-acetyl(2- aminoethyl)glycine through the N-acetyl
group at position 9 of the heterocycle."

(ix) FEATURE:
(A) NAME/KEY: Modified-site
(B) LOCATION: 15
(D) OTHER INFORMATION: /label=Modified-site
/ note= "Thymine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 16
(D) OTHER INFORMATION: /label=Modified-site
/ note= "Cytosine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 17

(D) OTHER INFORMATION: /label=Modified-site
/ note= "Guanine heterocycle is attached to
N-acetyl(2- aminoethyl)glycine through the N-acetyl
group at position 9 of the heterocycle."

(ix) FEATURE:
(A) NAME/KEY: Modified-site
(B) LOCATION: 18
(D) OTHER INFORMATION: /label=Modified-site
/ note= "Cytosine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 19
(D) OTHER INFORMATION: /label=Modified-site
/ note= "Thymine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 20
(D) OTHER INFORMATION: /label=Modified-site
/ note= "Cytosine heterocycle is attached to
N-acetyl(2- aminoethyl)glycine through the N-acetyl
group at position 1 of the heterocycle."

(xi) SEQUENCE DESCRIPTION: SEQ ID NO:18:

Xaa Xaa Xaa Xaa Xaa Xaa Xaa Xaa Xaa Xaa Xaa Xaa Xaa Xaa Xaa Xaa
1               5                           10                          15

Xaa Xaa Xaa Xaa Lys
            20

(2) INFORMATION FOR SEQ ID NO:19:

(i) SEQUENCE CHARACTERISTICS:
(A) LENGTH: 20 amino acids
(B) TYPE: amino acid
(C) STRANDEDNESS: single
(D) TOPOLOGY: unknown (ii) MOLECULE TYPE: peptide (ix) FEATURE:
(A) NAME/KEY: Modified-site
(B) LOCATION: 1
(D) OTHER INFORMATION: /label=Modified-site
/ note= "Cytosine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 2
(D) OTHER INFORMATION: /label=Modified-site
/ note= "Thymine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 3
(D) OTHER INFORMATION: /label=Modified-site
/ note= "Guanine heterocycle is attached to
N-acetyl(2- aminoethyl)glycine through the N-acetyl
group at position 9 of the heterocycle."

(ix) FEATURE:
(A) NAME/KEY: Modified-site
(B) LOCATION: 4
(D) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
                ( A ) NAME/KEY: Modified-site
                ( B ) LOCATION: 5
                ( D ) OTHER INFORMATION: /label=Modified-site
                        / note= "Cytosine heterocycle is attached to
                        N-acetyl(2- aminoethyl)glycine through the N-acetyl
                        group at position 1 of the heterocycle."

( i x ) FEATURE:
                ( A ) NAME/KEY: Modified-site
                ( B ) LOCATION: 6
                ( D ) OTHER INFORMATION: /label=Modified-site
                        / note= "Thymine heterocycle is attached to
                        N-acetyl(2- aminoethyl)glycine through the N-acetyl
                        group at position 1 of the heterocycle."

( i x ) FEATURE:
                ( A ) NAME/KEY: Modified-site
                ( B ) LOCATION: 7
                ( D ) OTHER INFORMATION: /label=Modified-site
                        / note= "Cytosine heterocycle is attached to
                        N-acetyl(2- aminoethyl)glycine through the N-acetyl
                        group at position 1 of the heterocycle."

( i x ) FEATURE:
                ( A ) NAME/KEY: Modified-site
                ( B ) LOCATION: 8
                ( D ) OTHER INFORMATION: /label=Modified-site
                        / note= "Cytosine heterocycle is attached to
                        N-acetyl(2- aminoethyl)glycine through the N-acetyl
                        group at position 1 of the heterocycle."

( i x ) FEATURE:
                ( A ) NAME/KEY: Modified-site
                ( B ) LOCATION: 9
                ( D ) OTHER INFORMATION: /label=Modified-site
                        / note= "Adenine heterocycle is attached to
                        N-acetyl(2- aminoethyl)glycine through the N-acetyl
                        group at position 9 of the heterocycle."

( i x ) FEATURE:
                ( A ) NAME/KEY: Modified-site
                ( B ) LOCATION: 10
                ( D ) OTHER INFORMATION: /label=Modified-site
                        / note= "Thymine heterocycle is attached to
                        N-acetyl(2- aminoethyl)glycine through the N-acetyl
                        group at position 1 of the heterocycle."

( i x ) FEATURE:
                ( A ) NAME/KEY: Modified-site
                ( B ) LOCATION: 11
                ( D ) OTHER INFORMATION: /label=Modified-site
                        / note= "Cytosine heterocycle is attached to
                        N-acetyl(2- aminoethyl)glycine through the N-acetyl
                        group at position 1 of the heterocycle."

( i x ) FEATURE:
                ( A ) NAME/KEY: Modified-site
                ( B ) LOCATION: 12
                ( D ) OTHER INFORMATION: /label=Modified-site
                        / note= "Cytosine heterocycle is attached to
                        N-acetyl(2- aminoethyl)glycine through the N-acetyl
                        group at position 1 of the heterocycle."

( i x ) FEATURE:
                ( A ) NAME/KEY: Modified-site
                ( B ) LOCATION: 13
                ( D ) OTHER INFORMATION: /label=Modified-site
                        / note= "Thymine heterocycle is attached to
                        N-acetyl(2- aminoethyl)glycine through the N-acetyl
                        group at position 1 of the heterocycle."

( i x ) FEATURE:
                ( A ) NAME/KEY: Modified-site
                ( B ) LOCATION: 14
                ( D ) OTHER INFORMATION: /label=Modified-site
                        / note= "Cytosine heterocycle is attached to
                        N-acetyl(2- aminoethyl)glycine through the N-acetyl
                        group at position 1 of the heterocycle."

( i x ) FEATURE:
- ( A ) NAME/KEY: Modified-site
- ( B ) LOCATION: 15
- ( D ) OTHER INFORMATION: /label=Modified-site
  / note= "Thymine heterocycle is attached to
  N-acetyl(2- aminoethyl)glycine through the N-acetyl
  group at position 1 of the heterocycle."

( i x ) FEATURE:
- ( A ) NAME/KEY: Modified-site
- ( B ) LOCATION: 16
- ( D ) OTHER INFORMATION: /label=Modified-site
  / note= "Thymine heterocycle is attached to
  N-acetyl(2- aminoethyl)glycine through the N-acetyl
  group at position 1 of the heterocycle."

( i x ) FEATURE:
- ( A ) NAME/KEY: Modified-site
- ( B ) LOCATION: 17
- ( D ) OTHER INFORMATION: /label=Modified-site
  / note= "Cytosine heterocycle is attached to
  N-acetyl(2- aminoethyl)glycine through the N-acetyl
  group at position 1 of the heterocycle."

( i x ) FEATURE:
- ( A ) NAME/KEY: Modified-site
- ( B ) LOCATION: 18
- ( D ) OTHER INFORMATION: /label=Modified-site
  / note= "Adenine heterocycle is attached to
  N-acetyl(2- aminoethyl)glycine through the N-acetyl
  group at position 9 of the heterocycle."

( i x ) FEATURE:
- ( A ) NAME/KEY: Modified-site
- ( B ) LOCATION: 19
- ( D ) OTHER INFORMATION: /label=Modified-site
  / note= "Cytosine heterocycle is attached to
  N-acetyl(2- aminoethyl)glycine through the N-acetyl
  group at position 1 of the heterocycle."

( i x ) FEATURE:
- ( A ) NAME/KEY: Modified-site
- ( B ) LOCATION: 20
- ( D ) OTHER INFORMATION: /label=Modified-site
  / note= "Thymine heterocycle is attached to
  N-acetyl(2- aminoethyl)glycine through the N-acetyl
  group at position 1 of the heterocycle."

( x i ) SEQUENCE DESCRIPTION: SEQ ID NO:19:

```
Xaa Xaa Xaa Xaa Xaa Xaa Xaa Xaa Xaa Xaa Xaa Xaa Xaa Xaa Xaa Xaa
1               5                   10                  15
Xaa Xaa Xaa Xaa
            20
```

( 2 ) INFORMATION FOR SEQ ID NO:20:

( i ) SEQUENCE CHARACTERISTICS:
- ( A ) LENGTH: 21 amino acids
- ( B ) TYPE: amino acid
- ( C ) STRANDEDNESS: single
- ( D ) TOPOLOGY: unknown ( i i ) MOLECULE TYPE: peptide ( i x ) FEATURE:
- ( A ) NAME/KEY: Modified-site
- ( B ) LOCATION: 1
- ( D ) OTHER INFORMATION: /label=Modified-site
  / note= "Thymine heterocycle is attached to
  N-acetyl(2- aminoethyl)glycine through the N-acetyl
  group at position 1 of the heterocycle."

( i x ) FEATURE:
- ( A ) NAME/KEY: Modified-site
- ( B ) LOCATION: 2
- ( D ) OTHER INFORMATION: /label=Modified-site
  / note= "Adenine heterocycle is attached to N-acetyl(2- aminoethyl)glycine through the N-acetyl
group at position 9 of the haterocycle."

( i x ) FEATURE:
    ( A ) NAME/KEY: Modified-site
    ( B ) LOCATION: 3
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 4
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 5
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 6
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 7
    ( D ) OTHER INFORMATION: /label=Modified-site
        / note= "Guanine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 8
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Adenine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 11
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 12
    ( D ) OTHER INFORMATION: /label=Modified-site
        / note= "Cytosine heterocycle is attached to -continued N-acetyl(2- aminoethyl)glycine through the N-acetyl
group at position 1 of the heterocycle."

( i x ) FEATURE:
    ( A ) NAME/KEY: Modified-site
    ( B ) LOCATION: 13
    ( D ) OTHER INFORMATION: /label=Modified-site
        / note= "Guanine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 14
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 15
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 16
    ( D ) OTHER INFORMATION: /label=Modified-site
        / note= "Cytosine heteroside is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 17
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 18
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 19
    ( D ) OTHER INFORMATION: /label=Modified-site
        / note= "Cytosine heterocycle is attached to
        N-acetyl(2- aminoethyl)glycine through the N-acetyl
        group at position 1 of thr heterocycle."

( i x ) FEATURE:
    ( A ) NAME/KEY: Modified-site
    ( B ) LOCATION: 20
    ( D ) OTHER INFORMATION: /label=Modified-site
        / note= "Adenine heterocycle is attached to
        N-acetyl(2- aminoethyl)glycine through the N-acetyl
        group at position 9 of the heterocycle."

( x i ) SEQUENCE DESCRIPTION: SEQ ID NO:20:

Xaa Xaa Xaa Xaa Xaa Xaa Xaa Xaa Xaa Xaa Xaa Xaa Xaa Xaa Xaa Xaa
1               5                           10                          15

Xaa Xaa Xaa Xaa Lys
            20

( 2 ) INFORMATION FOR SEQ ID NO:21:

( i ) SEQUENCE CHARACTERISTICS:
        ( A ) LENGTH: 20 amino acids

-continued

```
            ( B ) TYPE: amino acid
            ( C ) STRANDEDNESS: single
            ( D ) TOPOLOGY: unknown ( i i ) MOLECULE TYPE: peptide ( i x ) FEATURE:
            ( A ) NAME/KEY: Modified-site
            ( B ) LOCATION: 1
            ( D ) OTHER INFORMATION: /label=Modified-site
                    / note= "Cytosine heterocycle is attached to
                    N-acetyl(2- aminoethyl)glycine through the N-acetyl
                    group at position 1 of the heterocycle."

( i x ) FEATURE:
            ( A ) NAME/KEY: Modified-site
            ( B ) LOCATION: 2
            ( D ) OTHER INFORMATION: /label=Modified-site
                    / note= "Cytosine heterocycle is attached to
                    N-acetyl(2- aminoethyl)glycine through the N-acetyl
                    group at position 1 of the heterocycle."

( i x ) FEATURE:
            ( A ) NAME/KEY: Modified-site
            ( B ) LOCATION: 3
            ( D ) OTHER INFORMATION: /label=Modified-site
                    / note= "Cytosine heterocycle is attached to
                    N-acetyl(2- aminoethyl)glycine through the N-acetyl
                    group at position 1 of the heterocycle."

( i x ) FEATURE:
            ( A ) NAME/KEY: Modified-site
            ( B ) LOCATION: 4
            ( D ) OTHER INFORMATION: /label=Modified-site
                    / note= "Cytosine heterocycle is attached to
                    N-acetyl(2- aminoethyl)glycine through the N-acetyl
                    group at position 1 of the heterocycle."

( i x ) FEATURE:
            ( A ) NAME/KEY: Modified-site
            ( B ) LOCATION: 5
            ( D ) OTHER INFORMATION: /label=Modified-site
                    / note= "Cytosine heterocycle is attached to
                    N-acetyl(2- aminoethyl)glycine through the N-acetyl
                    group at position 1 of the heterocycle."

( i x ) FEATURE:
            ( A ) NAME/KEY: Modified-site
            ( B ) LOCATION: 6
            ( D ) OTHER INFORMATION: /label=Modified-site
                    / note= "Adenine heterocycle is attached to
                    N-acetyl(2- aminoethyl)glycine through the N-acetyl
                    group at position 9 of the heterocycle."

( i x ) FEATURE:
            ( A ) NAME/KEY: Modified-site
            ( B ) LOCATION: 7
            ( D ) OTHER INFORMATION: /label=Modified-site
                    / note= "Cytosine heterocycle is attached to
                    N-acetyl(2- aminoethyl)glycine through the N-acetyl
                    group at position 1 of the heterocycle."

( i x ) FEATURE:
            ( A ) NAME/KEY: Modified-site
            ( B ) LOCATION: 8
            ( D ) OTHER INFORMATION: /label=Modified-site
                    / note= "Cytosine heterocycle is attached to
                    N-acetyl(2- aminoethyl)glycine through the N-acetyl
                    group at position 1 of the heterocycle."

( i x ) FEATURE:
            ( A ) NAME/KEY: Modified-site
            ( B ) LOCATION: 9
            ( D ) OTHER INFORMATION: /label=Modified-site
                    / note= "Adenine heterocycle is attached to
                    N-acetyl(2- aminoethyl)glycine through the N-acetyl
                    group at position 9 of the heterocycle."

( i x ) FEATURE:
            ( A ) NAME/KEY: Modified-site
```

( B ) LOCATION: 10
( D ) OTHER INFORMATION: /label=Modified-site
/ note= "Cytosine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 11
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 12
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 13
( D ) OTHER INFORMATION: /label=Modified-site
/ note= "Cytosine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 14
( D ) OTHER INFORMATION: /label=Modified-site
/ note= "Cytosine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 15
( D ) OTHER INFORMATION: /label=Modified-site
/ note= "Cytosine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 16
( D ) OTHER INFORMATION: /label=Modified-site
/ note= "Cytosine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 17
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 18
( D ) OTHER INFORMATION: /label=Modified-site
/ note= "Cytosine heterocycle is attached to
N-acetyl(2- aminoethyl)glycine through the N-acetyl
group at position 1 of the heterocycle."

( i x ) FEATURE:
( A ) NAME/KEY: Modified-site
( B ) LOCATION: 19
( D ) OTHER INFORMATION: /label=Modified-site
/ note= "Thymine heterocycle is attached to
N-acetyl(2- aminoethyl)glycine through the N-acetyl
group at position 1 of the heterocycle."

( i x ) FEATURE:
( A ) NAME/KEY: Modified-site (B) LOCATION: 20
(D) OTHER INFORMATION: /label=Modified-site
/ note= "Cytosine heterocycle is attached to
N-acetyl(2- aminoethyl)glycine through the N-acetyl
group at position 1 of the heterocycle."

(xi) SEQUENCE DESCRIPTION: SEQ ID NO:21:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
        20

(2) INFORMATION FOR SEQ ID NO:22:

(i) SEQUENCE CHARACTERISTICS:
(A) LENGTH: 21 amino acids
(B) TYPE: amino acid
(C) STRANDEDNESS: single
(D) TOPOLOGY: unknown (ii) MOLECULE TYPE: peptide (ix) FEATURE:
(A) NAME/KEY: Modified-site
(B) LOCATION: 1
(D) OTHER INFORMATION: /label=Modified-site
/ note= "Cytosine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 2
(D) OTHER INFORMATION: /label=Modified-site
/ note= "Thymine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 3
(D) OTHER INFORMATION: /label=Modified-site
/ note= "Guanine heterocycle is attached to
N-acetyl(2- aminoethyl)glycine through the N-acetyl
group at position 9 of the heterocycle."

(ix) FEATURE:
(A) NAME/KEY: Modified-site
(B) LOCATION: 4
(D) OTHER INFORMATION: /label=Modified-site
/ note= "Cytosine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 5
(D) OTHER INFORMATION: /label=Modified-site
/ note= "Thymine heterocycle is attached to
N-acetyl(2- aminoethyl)glycine through the N-acetyl
group at position 1 of the heterocycle."

(ix) FEATURE:
(A) NAME/KEY: Modified-site
(B) LOCATION: 6
(D) OTHER INFORMATION: /label=Modified-site
/ note= "Guanine heterocycle is attached to
N-acetyl(2- aminoethyl)glycine through the N-acetyl
group at position 9 of the heterocycle."

(ix) FEATURE:
(A) NAME/KEY: Modified-site
(B) LOCATION: 7
(D) OTHER INFORMATION: /label=Modified-site
/ note= "Cytosine heterocycle is attached to
N-acetyl(2- aminoethyl)glycine through the N-acetyl
group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 11
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 12
    ( D ) OTHER INFORMATION: /label=Modified-site
        / note= "Guanine heterocycle is attached to
        N-acetyl(2- aminoethyl)glycine through the N-acetyl
        group at position 9 of the heterocycle."

( i x ) FEATURE:
    ( A ) NAME/KEY: Modified-site
    ( B ) LOCATION: 13
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 14
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 15
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 16
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 17
    ( D ) OTHER INFORMATION: /label=Modified-site
        / note= "Adenine heterocycle is attached to
        N-acetyl(2- aminoethyl)glycine through the N-acetyl
        group at position 9 of the heterocycle."

(ix) FEATURE:
    (A) NAME/KEY: Modified-site
    (B) LOCATION: 18
    (D) OTHER INFORMATION: /label=Modified-site
        /note= "Guanine heterocycle is attached to
        N-acetyl(2- aminoethyl)glycine through the N-acetyl
        group at position 9 of the heterocycle."

(ix) FEATURE:
    (A) NAME/KEY: Modified-site
    (B) LOCATION: 19
    (D) OTHER INFORMATION: /label=Modified-site
        /note= "Guanine heterocycle is attached to
        N-acetyl(2- aminoethyl)glycine through the N-acetyl
        group at position 9 of the heterocycle."

(ix) FEATURE:
    (A) NAME/KEY: Modified-site
    (B) LOCATION: 20
    (D) OTHER INFORMATION: /label=Modified-site
        /note= "Thymine heterocycle is attached to
        N-acetyl(2- aminoethyl)glycine through the N-acetyl
        group at position 1 of thr heterocycle."

(xi) SEQUENCE DESCRIPTION: SEQ ID NO:22:

Xaa Xaa Xaa Xaa Xaa Xaa Xaa Xaa Xaa Xaa Xaa Xaa Xaa Xaa Xaa Xaa
1                  5                              10                            15

Xaa Xaa Xaa Xaa Lys
           20

(2) INFORMATION FOR SEQ ID NO:23:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label=Modified-site
            /note= "Thymine heterocycle is attached to
            N-acetyl(2- aminoethyl)glycine through the N-acetyl
            group at position 1 of the heterocycle."

(ix) FEATURE:
        (A) NAME/KEY: Modified-site
        (B) LOCATION: 2
        (D) OTHER INFORMATION: /label=Modified-site
            /note= "Thymine heterocycle is attached to
            N-acetyl(2- aminoethyl)glycine through the N-acetyl
            group at position 1 of the heterocycle."

(ix) FEATURE:
        (A) NAME/KEY: Modified-site
        (B) LOCATION: 3
        (D) OTHER INFORMATION: /label=Modified-site
            /note= "Thymine heterocycle is attached to
            N-acetyl(2- aminoethyl)glycine through the N-acetyl
            group at position 1 of the heterocycle."

(ix) FEATURE:
        (A) NAME/KEY: Modified-site
        (B) LOCATION: 4
        (D) OTHER INFORMATION: /label=Modified-site
            /note= "Thymine heterocycle is attached to
            N-acetyl(2- aminoethyl)glycinr through the N-acetyl
            group at position 1 of the heterocycle."

(ix) FEATURE:
        (A) NAME/KEY: Modified-site
        (B) LOCATION: 5
        (D) OTHER INFORMATION: /label=Modified-site / note= "Beta isoform of alanine."

( i x ) FEATURE:
    ( A ) NAME/KEY: Modified-site
    ( B ) LOCATION: 6
    ( D ) OTHER INFORMATION: /label=Modified-site
        / note= "Cytosine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 11
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( x i ) SEQUENCE DESCRIPTION: SEQ ID NO:23:

```
Xaa  Xaa  Xaa  Xaa  Ala  Xaa  Xaa  Xaa  Xaa  Xaa  Xaa  Lys
1                  5                        10
```

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Thymine heterocycle is attached to
            N-acetyl(2- aminoethyl)glycine through the N-acetyl
            group at position 1 of the heterocycle."

( i x ) FEATURE:
        ( A ) NAME/KEY: Modified-site
        ( B ) LOCATION: 2
        ( D ) OTHER INFORMATION: /label=Modified-site
            / note= "Thymine heterocycle is attached to
            N-acetyl(2- aminoethyl)glycine through the N-acetyl -continued group at position 1 of the heterocycle."

( i x ) FEATURE:
    ( A ) NAME/KEY: Modified-site
    ( B ) LOCATION: 3
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 4
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 5
    ( D ) OTHER INFORMATION: /label=Modified-site
        / note= "Beta isoform of alanine."

( i x ) FEATURE:
    ( A ) NAME/KEY: Modified-site
    ( B ) LOCATION: 6
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 7
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 8
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 9
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 10
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( i x ) FEATURE:
    ( A ) NAME/KEY: Modified-site
    ( B ) LOCATION: 11
    ( D ) OTHER INFORMATION: /label=Modified-site
        / note= "Thymine heterocycle is attached to
        N-acetyl(2- aminoethyl)glycine through the N-acetyl
        group at position 1 of the heterocycle."

( x i ) SEQUENCE DESCRIPTION: SEQ ID NO:24:

```
Xaa  Xaa  Xaa  Xaa  Ala  Xaa  Xaa  Xaa  Xaa  Xaa  Xaa  Lys
1                  5                        10
```

PEPTIDE NUCLEIC ACIDS

RELATED APPLICATION

This application is a division of U.S. application Ser. No. 08/054,363 filed Apr. 26, 1993 (now U.S. Pat. No. 5,539,082), which is a continuation-in-part of U.S. application Ser. No. 08/108,591 filed Nov. 22, 1993, which, in turn, is the U.S. national phase of PCT Application EP92/01219, filed May 22, 1992 and published on Nov. 26, 1992, as WO 92/20702 (now abandoned).

FIELD OF THE INVENTION

This invention is directed to compounds that are not polynucleotides yet which bind to complementary DNA and RNA strands. In particular, the invention concerns compounds wherein naturally-occurring nucleobases or other nucleobase-binding moieties are covalently bound to a polyamide backbone.

BACKGROUND OF THE INVENTION

Oligodeoxyribonucleotides as long as 100 base pairs (bp) are routinely synthesized by solid phase methods using commercially available, fully automatic synthesis machines. The chemical synthesis of oligoribonucleotides, however, is far less routine. Oligoribonucleotides also are much less stable than oligodeoxyribonucleotides, a fact which has contributed to the more prevalent use of oligodeoxyribonucleotides in medical and biological research directed to, for example, gene therapy or the regulation of transcription or translation.

The function of a gene starts by transcription of its information to a messenger RNA (mRNA) which, by interaction with the ribosomal complex, directs the synthesis of a protein coded for by its sequence. The synthetic process is known as translation. Translation requires the presence of various co-factors and building blocks, the amino acids, and their transfer RNAs (tRNA), all of which are present in normal cells.

Transcription initiation requires specific recognition of a promoter DNA sequence by the RNA-synthesizing enzyme, RNA polymerase. In many cases in prokaryotic cells, and probably in all cases in eukaryotic cells, this recognition is preceded by sequence-specific binding of a protein transcription factor to the promoter. Other proteins which bind to the promoter, but whose binding prohibits action of RNA polymerase, are known as repressors. Thus, gene activation typically is regulated positively by transcription factors and negatively by repressors.

Most conventional drugs function by interaction with and modulation of one or more targeted endogenous proteins, e.g., enzymes. Such drugs, however, typically are not specific for targeted proteins but interact with other proteins as well. Thus, a relatively large dose of drug must be used to effectively modulate a targeted protein. Typical daily doses of drugs are from $10^{-5}$–$5^{-1}$ millimoles per kilogram of body weight or $10^{-3}$–10 millimoles for a 100 kilogram person. If this modulation instead could be effected by interaction with and inactivation of mRNA, a dramatic reduction in the necessary amount of drug necessary could likely be achieved, along with a corresponding reduction in side effects. Further reductions could be effected if such interaction could be rendered site- specific. Given that a functioning gene continually produces mRNA, it would thus be even more advantageous if gene transcription could be arrested in its entirety.

Oligodeoxynucleotides offer such opportunities. For example, synthetic oligodeoxynucleotides could be used as antisense probes to block and eventually lead to the breakdown of mRNA. Thus, synthetic DNA could suppress translation in vivo. It also may be possible to modulate the genome of an animal by, for example, triple helix formation using oligonucleotides or other DNA recognizing agents. However, there are a number of drawbacks associated with triple helix formation. For example, it can only be used for homopurine sequences and it requires unphysiologically high ionic strength and low pH.

Furthermore, unmodified oligonucleotides are unpractical both in the antisense approach and in the triple helix approach because they have short in vivo half-lives, they are difficult to prepare in more than milligram quantities and, thus, are prohibitively costly, and they are poor cell membrane penetrators.

These problems have resulted in an extensive search for improvements and alternatives. For example, the problems arising in connection with double-stranded DNA (dsDNA) recognition through triple helix formation have been diminished by a clever "switch back" chemical linking whereby a sequence of polypurine on one strand is recognized, and by "switching back", a homopurine sequence on the other strand can be recognized. See, e.g., McCurdy, Moulds, and Froehler, Nucleosides Nucleotides 1991 10, 287. Also, good helix formation has been obtained by using artificial bases, thereby improving binding conditions with regard to ionic strength and pH.

In order to improve half life as well as membrane penetration, a large number of variations in polynucleotide backbones has been undertaken, although so far not with the desired results. These variations include the use of methylphosphonates, monothiophosphates, dithiophosphates, phosphoramidates, phosphate esters, bridged phosphoroamidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAs, α-anomeric bridges, and borane derivatives.

The great majority of these backbone modifications led to decreased stability for hybrids formed between the modified oligonucleotide and its complementary native oligonucleotide, as assayed by measuring $T_m$ values. Consequently, it is generally understood in the art that backbone modifications destabilize such hybrids, i.e., result in lower $T_m$ values, and should be kept to a minimum.

OBJECTS OF THE INVENTION

It is one object of the present invention to provide compounds that bind ssDNA and RNA strands to form stable hybrids therewith.

It is a further object of the invention to provide compounds that bind ssDNA and RNA strands.

It is another object to provide compounds wherein naturally-occurring nucleobases or other nucleobase-binding moieties are covalently bound to a peptide backbone.

It is yet another object to provide compounds other than RNA that can bind one strand of a double-stranded polynucleotide, thereby displacing the other strand.

It is still another object to provide therapeutic, diagnostic, and prophylactic methods that employ such compounds.

SUMMARY OF THE INVENTION

The present invention provides a novel class of compounds, known as peptide nucleic acids (PNAs), that bind complementary ssDNA and RNA strands. The compounds of the invention generally comprise ligands linked to a peptide backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker.

In WO 92/20702, we described PNAs wherein such ligands are linked to a polyamide backbone solely through aza nitrogen atoms. The PNAs of the invention differ from those disclosed in WO 92/20702 principally in that their recognition moieties are linked to the polyamide backbone additionally through amido and/or ureido tethers.

In certain preferred embodiments, the peptide nucleic acids of the invention have the general formula (I):

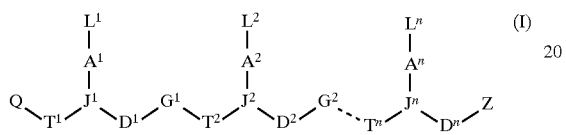

wherein:
n is at least 2,
each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands, at least one of $L^1$–$L^n$ being a naturally occurring nucleobase, a non-naturally occurring nucleobase, a DNA intercalator, or a nucleobase-binding group;
each of $T^1$–$T^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$) alkoxy, ($C_1$–$C_6$) alkylthio, $NR^3R^4$ and $SR^5$, where $R^3$ and $R^4$ are as defined below, and $R^5$ is hydrogen, ($C_1$–$C_6$) alkyl, hydroxy-, alkoxy-, or alkylthio- substituted ($C_1$–$C_6$) alkyl, or $R^6$ and $R^7$ taken together complete an alicyclic or heterocyclic system;
each of $D^1$–$D^n$ is $(CR^6R^7)_z$ where $R^6$ and $R^7$ are as defined above;
each of y and z is zero or an integer from 1 to 10, the sum y+z being greater than 2 but not more than 10;
each of $G^1$–$G^{n-1}$ is —$NR^3CO$—, —$NR^3CS$—, —$NR^3SO$— or —$NR^3SO_2$—, in either orientation, where $R^3$ is as defined above;
each pair of $A^1$–$A^n$ and $J^1$–$J^n$ are selected such that:
(a) A is a group of formula (IIa), (IIb) or (IIc) and J is N or $R^3N^+$; or
(b) A is a group of formula (IId) and J is CH;

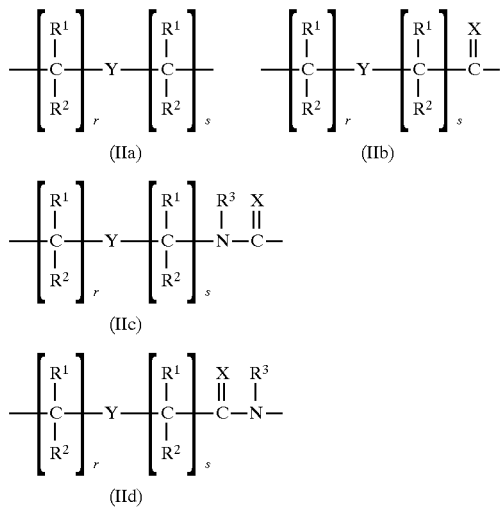

where:

X is O, S, Se, $NR^3$, $CH_2$ or $C(CH_3)_2$;

Y is a single bond, O, S or $NR^4$;

each of r and s is zero or an integer from 1 to 5, the sum r+s being not more than 10;

each $R^1$ and $R^2$ is independently selected from the group consisting of hydrogen, ($C_1$–$C_4$) alkyl which may be hydroxy- or alkoxy- or alkylthio-substituted, hydroxy, alkoxy, alkylthio, amino and halogen;

each of $G^1$–$G^{n-1}$ is —$NR^3CO$—, —$NR^3CS$—, —$NR^3SO$— or —$NR^3SO_2$—, in either orientation, where $R^3$ is as defined above;

Q is —$CO_2H$, —$CONR^8R^9$, —$SO_3H$ or —$SO_2NR^8R^9$ or an activated derivative of —$CO_2H$ or —$SO_3H$; and Z is —$NHR^{10}R^{11}$ or —$NR^{10}C(O)R^{11}$, where $R^8$, $R^9$, $R^{10}$ and $R^{11}$ are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers.

In certain embodiments, at least one A is a group of formula (IIc) and J is N or $R^3N^+$. In other embodiments, A is a group of formula (IIa) or (IIb), J is N or $R^3N^+$, and at least one of y or z is not 1 or 2.

Preferred peptide nucleic acids have general formula (IIIa) or (IIIb):

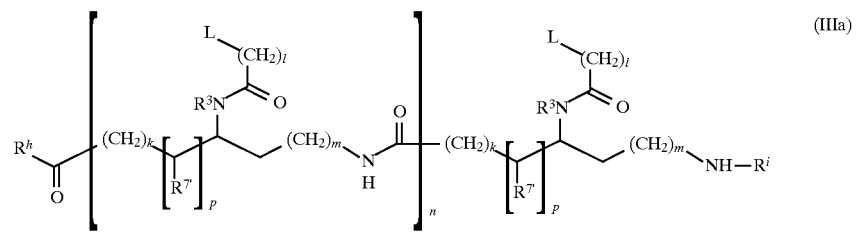

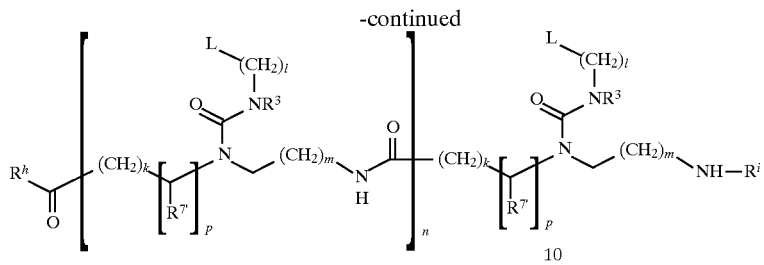

wherein:

each L is independently selected from the group consisting of hydrogen, phenyl, heterocyclic moieties, naturally occurring nucleobases, and non-naturally occurring nucleobases;

each $R^{7'}$ is independently selected from the group consisting of hydrogen and the side chains of naturally occurring alpha amino acids;

n is an integer from 1 to 60;

each of k, l, and m is independently zero or an integer from 1 to 5;

p is zero or 1;

$R^h$ is OH, $NH_2$ or —$NHLysNH_2$; and $R^i$ is H or $COCH_3$.

Particularly preferred are compounds having formula (IIIa) or (IIIb) wherein each L is independently selected from the group consisting of the nucleobases thymine (T), adenine (A), cytosine (C), guanine (G) and uracil (U), k and m are zero or 1, and n is an integer from 1 to 30, in particular from 4 to 20.

The peptide nucleic acids of the invention are synthesized by adaptation of standard peptide synthesis procedures, either in solution or on a solid phase. The synthons used are specially monomer amino acids or their activated derivatives, protected by standard protecting groups. The oligonucleotide analogs also can be synthesized by using the corresponding diacids and diamines.

Thus, the novel monomer synthons according to the invention are selected from the group consisting of amino acids, diacids and diamines having general formulae:

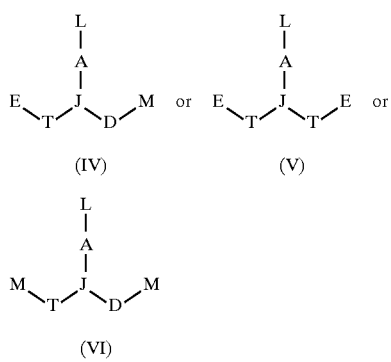

wherein L, A, J, T and D are as defined above, except that any amino groups therein may be protected by amino protecting groups; E is COOH, CSOH, SOOH, $SO_2OH$ or an activated derivative thereof; and M is $NHR^3$ or $NR^3R^{12}$, where $R^3$ is as defined above and $R^{12}$ is an amino protecting group.

Preferred monomer synthons according to the invention have formula (VIIIa)–(VIIIc):

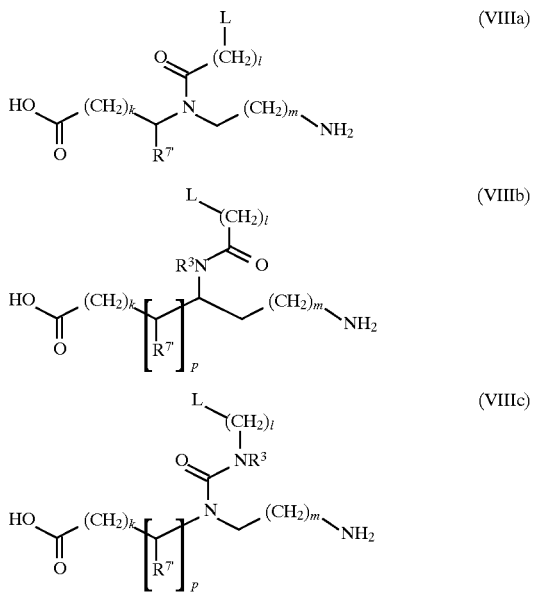

or amino-protected and/or acid terminal activated derivatives thereof, wherein L is selected from the group consisting of hydrogen, phenyl, heterocyclic moieties, naturally occurring nucleobases, and non-naturally occurring nucleobases; and $R^{7'}$ is selected from the group consisting of hydrogen and the side chains of naturally occurring alpha amino acids.

Unexpectedly, these compounds also are able to recognize duplex DNA by displacing one strand, thereby presumably generating a double helix with the other one. Such recognition can take place to dsDNA sequences 5–60 base pairs long. Sequences between 10 and 20 bases are of interest since this is the range within which unique DNA sequences of prokaryotes and eukaryotes are found. Reagents which recognize 17–18 bases are of particular interest since this is the length of unique sequences in the human genome. The compounds of the invention are able to form triple helices with dsDNA and double helices with RNA or ssDNA. The compounds of the invention also are able to form triple helices wherein a first PNA strand binds with RNA or ssDNA and a second PNA strand binds with the resulting double helix or with the first PNA strand.

Whereas the improved binding of the compounds of the invention should render them efficient as antisense agents, it is expected that an extended range of related reagents may cause strand displacement, now that this surprising and unexpected new behavior of dsDNA has been discovered.

Thus, in one aspect, the present invention provides methods for inhibiting the expression of particular genes in the cells of an organism, comprising administering to said organism a reagent as defined above which binds specifically to sequences of said genes.

Further, the invention provides methods for inhibiting transcription and/or replication of particular genes or for inducing degradation of particular regions of double stranded DNA in cells of an organism by administering to said organism a reagent as defined above.

Still further, the invention provides methods for killing cells or virus by contacting said cells or virus with a reagent as defined above which binds specifically to sequences of the genome of said cells or virus.

DETAILED DESCRIPTION OF THE INVENTION

In the oligonucleotide analogs and monomer synthons according to the invention, ligand L is primarily a naturally occurring nucleobase attached at the position found in nature, i.e., position 9 for adenine or guanine, and position 1 for thymine or cytosine. Alternatively, L may be a non-naturally occurring nucleobase (nucleobase analog), another base-binding moiety, an aromatic moiety, $(C_1–C_4)$alkanoyl, hydroxy or even hydrogen. It will be understood that the term nucleobase includes nucleobases bearing removable protecting groups. Some typical nucleobase ligands and illustrative synthetic ligands are shown in FIG. 2 of WO 92/20702. Furthermore, L can be a DNA intercalator, a reporter ligand such as, for example, a fluorophor, radio label, spin label, hapten, or a protein-recognizing ligand such as biotin. In monomer synthons, L may be blocked with protecting groups, as illustrated in FIG. 4 of WO 92/20702.

Linker A can be a wide variety of groups such as —$CR^1R^2CO$—, —$CR^1R^2CS$—, —$CR^1R^2CSe$—, —$CR^1R^2CNHR^3$—, —$CR^1R^2C{=}CH_2$— and —$CR^1R^2C{=}C(CH_3)_2$—, where $R^1$, $R^2$ and $R^3$ are as defined above. Preferably, A is methylenecarbonyl (—$CH_2CO$—), amido (—$CONR^3$—), or ureido (—$NR^3CONR^3$—). Also, A can be a longer chain moiety such as propanoyl, butanoyl or pentanoyl, or corresponding derivative, wherein O is replaced by another value of X or the chain is substituted with $R^1R^2$ or is heterogenous, containing Y. Further, A can be a $(C_2–C_6)$alkylene chain, a $(C_2–C_6)$ alkylene chain substituted with $R^1R^2$ or can be heterogenous, containing Y. In certain cases, A can just be a single bond.

In one preferred form of the invention, B is a nitrogen atom, thereby presenting the possibility of an achiral backbone. B can also be $R^3N^+$, where $R^3$ is as defined above, or CH.

In the preferred form of the invention, C is —$CR^6R^7$—, but can also be a two carbon unit, i.e. —$CHR^6CHR^7$— or —$CR^6R^7CH_2$—, where $R^6$ and $R^7$ are as defined above. $R^6$ and $R^7$ also can be a heteroaryl group such as, for example, pyrrolyl, furyl, thienyl, imidazolyl, pyridyl, pyrimidinyl, indolyl, or can be taken together to complete an alicyclic system such as, for example, 1,2-cyclobutanediyl, 1,2-cyclopentanediyl or 1,2-cyclohexanediyl.

In the preferred form of the invention, E in the monomer synthon is COOH or an activated derivative thereof, and G in the oligomer is —$CONR^3$—. As defined above, E may also be CSOH, SOOH, $SO_2OH$ or an activated derivative thereof, whereby G in the oligomer becomes —$CSNR^3$—, —$SONR^3$— and —$SO_2NR^3$—, respectively. The activation may, for example, be achieved using an acid anhydride or an active ester derivative, wherein hydrogen in the groups represented by E is replaced by a leaving group suited for generating the growing backbone.

The amino acids which form the backbone may be identical or different. We have found that those based on 2-aminoethylglycine are especially well suited to the purpose of the invention.

In some cases it may be of interest to attach ligands at either terminus (Q, I) to modulate the binding characteristics of the PNAs. Representative ligands include DNA intercalators which will improve dsDNA binding or basic groups, such as lysine or polylysine, which will strengthen the binding of PNA due to electrostatic interaction. To decrease negatively charged groups such as carboxy and sulfo groups could be used. The design of the synthons further allows such other moieties to be located on non-terminal positions.

In a further aspect of the invention, the PNA oligomers are conjugated to low molecular effector ligands such as ligands having nuclease activity or alkylating activity or reporter ligands (fluorescent, spin labels, radioactive, protein recognition ligands, for example, biotin or haptens). In a further aspect of the invention, the PNAs are conjugated to peptides or proteins, where the peptides have signaling activity and the proteins are, for example, enzymes, transcription factors or antibodies. Also, the PNAs can be attached to water-soluble or water-insoluble polymers. In another aspect of the invention, the PNAs are conjugated to oligonucleotides or carbohydrates. When warranted, a PNA oligomer can be synthesized onto some moiety (e.g., a peptide chain, reporter, intercalator or other type of ligand-containing group) attached to a solid support.

Such conjugates can be used for gene modulation (e.g., gene targeted drugs), for diagnostics, for biotechnology, and for scientific purposes.

As a further aspect of the invention, PNAs can be used to target RNA and ssDNA to produce both antisense-type gene regulating moieties and hybridization probes for the identification and purification of nucleic acids. Furthermore, the PNAs can be modified in such a way that they can form triple helices with dsDNA. Reagents that bind sequence-specifically to dsDNA have applications as gene targeted drugs. These are foreseen as extremely useful drugs for treating diseases like cancer, AIDS and other virus infections, and may also prove effective for treatment of some genetic diseases. Furthermore, these reagents may be used for research and in diagnostics for detection and isolation of specific nucleic acids.

The triple helix principle is believed to be the only known principle in the art for sequence-specific recognition of dsDNA. However, triple helix formation is largely limited to recognition of homopurine-homopyrimidine sequences. Strand displacement is superior to triple helix recognition in that it allows for recognition of any sequence by use of the four natural bases. Also, in strand displacement recognition readily occurs at physiological conditions, that is, neutral pH, ambient (20°–40° C.) temperature and medium (100–150 mM) ionic strength.

Gene targeted drugs are designed with a nucleobase sequence (containing 10–20 units) complementary to the regulatory region (the promoter) of the target gene. Therefore, upon administration of the drug, it binds to the promoter and blocks access thereto by RNA polymerase. Consequently, no mRNA, and thus no gene product (protein), is produced. If the target is within a vital gene for a virus, no viable virus particles will be produced. Alternatively, the target could be downstream from the promoter, causing the RNA polymerase to terminate at this position, thus forming a truncated mRNA/protein which is nonfunctional.

Sequence-specific recognition of ssDNA by base complementary hybridization can likewise be exploited to target specific genes and viruses. In this case, the target sequence is contained in the mRNA such that binding of the drug to the target hinders the action of ribosomes and, consequently, translation of the mRNA into protein. The peptide nucleic acids of the invention are superior to prior reagents in that they have significantly higher affinity for complementary ssDNA. Also, they possess no charge and are water soluble, which should facilitate cellular uptake, and they contain amides of non-biological amino acids, which should make them biostable and resistant to enzymatic degradation by, for example, proteases.

It is believed that PNA oligomers according to the invention exhibit biochemical/biological properties similar to those disclosed in WO 92/20702, and that such properties can be determined by similar means. It also is believed that the PNAs of the invention can be synthesized by similar methodology. Monomer synthons according to the invention are coupled using the standard protocols to give the desired oligomeric sequences.

One monomer synthon according to the invention is prepared by reacting glycinamide hydrochloride 1 with ethyl acrylate in the presence of an acid scavenging base to give the Michael adduct, N-carboxamidomethyl-β-alanine ethyl ester 2. The adduct 2 is condensed with 1-carboxymethyl thymine 3 using diisopropylcarbodiimide and hydroxybenzotriazole to give (N-carboxamidomethyl)-N-(1-(thymin-1-yl)acetyl)-β-alanine ethyl ester 4. The primary amide of 4 is oxidized and rearranged to the Boc-protected amine with sodium hypobromite in t-butanol to provide (N-t-butyloxycarbonylaminomethyl)-N-(1-(thymin-1-yl)acetyl)-β-alanine ethyl ester 5. The ethyl ester is hydrolyzed with aqueous base to provide the thymine-based monomer, (N-t-butyloxycarbonylaminomethyl)-N-(1-(thymin-1-yl)acetyl)-β-alanine 6. This reaction sequence is followed to prepare the corresponding C, G, and A -based monomers, namely, N-(t-butyloxycarbonylaminomethyl)-N-(1-($N^4$-benzyloxycarbonyl-cytosin-1-yl)acetyl)-β-alanine, N-(t-butyloxycarbonyl- aminomethyl-N-(1-(2-amino-6-benzyloxy-purin-9-yl) acetyl) -β-alanine, N-(t-butyloxycarbonylaminomethyl)-N-(1-($N^6$-benzyloxycarbonyl-adenine-9-yl)acetyl)-β-alanine.

A further monomer synthon is prepared by reacting 1-aminothymine with triphosgene to give the carbamoyl chloride derivative, 8, which is condensed with N-(2-t-butyloxycarbonylaminoethyl)glycine ethyl ester and an acid scavenger to yield the fully protected monomer, 9. The ester is hydrolyzed to give the useful monomer, 10. This reaction sequence is followed to prepare the corresponding C, G, and A -based monomers, namely, N-(t-butyloxycarbonylaminoethyl)-N-(1-$N^4$-benzyloxycarbonyl-cytosin-1-yl)aminocarbonyl)-glycine, N-(t-butyloxycarbonylaminoethyl)-N-(1-(2-amino-6-benzyloxy-purin-9-yl)-aminocarbonyl)-glycine, N-(t-butyloxycarbonyl-amino ethyl)-N-(1-($N^6$-benzyloxycarbonyl-adenine-9-yl)aminocarbonyl)-glycine.

A further monomer synthon is prepared by converting 2-hydroxy-5- (t-butyloxycarbonylamino) pentanoic acid ethyl ester to its azido analog via the use of diphenyl phosphoryl azide, DEAD, and triphenylphosphine generally by the procedure described in Tetrahedron Letters, (1977), p. 1977. The azido compound, 12, was converted to the iminophosphorane, 13, and used immediately in a high pressure reaction with carbon dioxide to convert it into isocyanate, 14. The isocyanate is condensed with thymine to give the fully protected monomer, 15, which is hydrolyzed to the actual monomer, 16, using hydroxide. This reaction sequence is followed to prepare the corresponding C, G, and A -based monomers, namely, 5-(t-butyloxycarbonylamino) -2-(($N^4$-benzyloxycarbonyl-cytosin-1-yl)carbonylamino-pentanoic acid ethyl ester, 5-(t-butyloxycarbonylamino-2-( (2-amino-6-benzyloxy-purin-9-yl)carbonylamino)- pentanoic acid ethyl ester, 5-(t-butyloxycarbonylamino)-2-( ($N^6$-benzyloxycarbonyl-adenine-9-yl)carbonylamino)- pentanoic acid ethyl ester.

Additional objects, advantages, and novel features of this invention will become apparent to those skilled in the art upon examination of the following examples thereof, which are not intended to be limiting.

EXAMPLE 1

N-carboxamidomethyl-β-alanine ethyl ester, 2.

Glycinamide hydrochloride (1, 11.0 g, 0.10 mol) is suspended in 500 mL of dioxane and diisopropylethylamine (12.9 g, 0.10 mol) is added and the mixture cooled to 0° C. With stirring ethyl acrylate (10.0 g, 0.10 mol) is added dropwise over 15 minutes. After the addition is complete the reaction is allowed to warm to room temperature and stir for 12 hours. The reaction mixture is diluted with water 1.5 L and the pH adjusted to 4. The solution is extracted with diethyl ether (3×300 mL) . The aqueous layer is neutralized with sodium hydroxide and extracted 5 times with dichloromethane. The dichloromethane extracts are combined, dried ($Na_2SO_4$), and the solvent removed to give a solid.

EXAMPLE 2

(N-carboxamidomethyl)-N-(1-(thymin-1-yl)acetyl)-β-alanine ethyl ester, 4.

The product from Example 1, 2, is dissolved in dichloromethane (500 mL) and to this is added 1-carboxymethyl thymine (3, 15.5 g, 0.1 mol), hydroxybenzotriazole (13.5 g, 0.1 mol) and the solution is cooled to 0° C. in an ice bath. Diisopropylcarbodiimide (12.6 g, 0.1 mol) dissolved in So mL of dichloromethane is added in one portion and the reaction is stirred for 12 hours. The suspended solids are removed by filtration and washed with dichloromethane. The solution is evaporated to a solid and the desired product, 4, is obtained after chromatography on silica gel using dichloromethane/ethanol as eluent.

EXAMPLE 3

(N-t-butyloxycarbonylaminomethyl)-N-(1-(thymin-1-yl)acetyl)-β-alanine ethyl ester, 5.

The product from Example 2, 4, is dissolved t-butanol/dioxane (4:1, 500 mL), cooled to 0° C., and sodium hypobromite solution (0.15 mol) is added. After 6 hours the reaction mixture is evaporated to remove volatile solvents and the residue is diluted with water (500 mL) and extracted (5×200 mL) with dichloromethane. The extracts are combined, dried, and evaporated to a solid.

EXAMPLE 4

(N-t-butyloxycarbonylaminomethyl)-N-(1-(thymin-1-yl)acetyl)-β-alanine, 6.

The product from Example 3, 5, is dissolved in ethanol (500 mL) and 5M sodium hydroxide (20 mL) is added. The solution is stirred for 6 hours, then neutralized with 5N hydrochloric acid (20 mL) and the solution evaporated to a solid. This solid is recrystallized to give the title compound.

EXAMPLE 5

1-(Chlorocarbonylamino)-thymine, 8.

1-Amino thymine (7, 12.5 g, 0.1 mol) is dissolved in tetrahydrofuran (500 mL) and the solution is cooled to 0° C.

and a 2M solution of triphosgene in THF (150 mL) is added and the reaction is stirred for 4 hours. The solution is evaporated to a solid, which is used as is in the next reaction.

EXAMPLE 6

N-(2-t-Butyloxycarbonylaminoethyl)-N-(thymin-1-yl-amino-carbonyl)glycine ethyl ester, 9.

The product from Example 5, 8, is dissolved in THF (500 mL) and diisopropylethylamine (12.9 g, 0.1 mol) is added, followed by N-(2-t-butyloxycarbonylaminoethyl)glycine ethyl ester (24.6 g, 0.1 mol) and the solution stirred for 12 hours. The reaction is diluted with 1000 mL of diethyl ether and extracted 3 times with 0.1N HCl solution. The organic layer is washed with diluted sodium bicarbonate solution, dried, filtered and evaporated to give a solid.

EXAMPLE 7

N-(2-t-Butyloxycarbonylaminoethyl)-N-(thymin-1-yl-amino-carbonyl)glycine, 10.

The product from Example 6, 9, is dissolved in ethanol (500 mL) and 2M sodium hydroxide (50 mL) is added. The reaction is stirred for 6 hours, then neutralized with 50 mL of 2M HCl solution, and evaporated to remove the ethanol. The residue is dissolved in dichloromethane (250 mL) and is extracted with water (2×50 mL), dried, filtered, and evaporated to a solid.

EXAMPLE 8

2-Azido-5-(t-butyloxycarbonylamino)pentanoic acid ethyl ester, 12.

2-Hydroxy-5-(t-butyloxycarbonylamino)pentanoic acid ethyl ester, (11, 26.1 g, 0.1 mol), triphenylphosphine (26.2 g, 0.10 mol), diethylazodicarboxylate (17.4 g, 0.1 mol), and diphenylphosphorylazide (27.5 g, 0.1 mol) is dissolved in THF (500 mL) and heated to reflux and maintained there for 8 hours. The reaction is cooled to room temperature, evaporated to an oil, and the product isolated by column chromatography using dichloromethane:ethanol as eluent.

EXAMPLE 9

2-Iminotriphenylphosphoranyl-5-(t-butyloxycarbonylamino)pentanoic acid ethyl ester, 13.

The product, 12, from Example 8 is dissolved in THF and triphenylphosphine (26.2 g, 0.1 mol) is added and the reaction is stirred for 4 hours. This solution is used as is for the next reaction (Example 10).

EXAMPLE 10

2-Isocyanato-5-(t-butyloxycarbonylamino)pentanoic acid ethyl ester, 14.

The reaction solution from Example 9 is placed in a Parr® bomb and carbon dioxide (22 g, 0.5 mol) is condensed into the bomb. The bomb is sealed and heated to 50° C. for 12 hours. The bomb is cooled and vented to atmospheric pressure. The solution is transferred from the bomb to a flask and used as is in the next reaction (Example 11).

EXAMPLE 11

2-(Thymin-1-ylcarbonylamino)-5-(t-butyloxycarbonylamino)pentanoic acid ethyl ester, 15.

The reaction solution from Example 10 is placed in a flask and to this is added thymine (12.6 g, 0.1 mol). The resulting solution is allowed to stir for 12 hours, then is evaporated to a solid, which is purified by column chromatography using dichlormethane:ethanol as the eluent.

EXAMPLE 12

2-(Thymin-1-ylcarbonylamino)-5-(t-butyloxycarbonyl-amino)pentanoic acid, 16.

The product from Example 11, 15, is dissolved in ethanol (500 mL) and to this added 2M sodium hydroxide (50 mL) and the reaction stirred for 12 hours. The reaction is neutralized with 2M HCl solution (50 mL) and evaporated to a small volume. This residue is diluted with water (250 mL) and extracted with dichloromethane (4×100 mL), dried, filtered, and evaporated to give a solid.

EXAMPLE 13

1-(2(-Thyminyl)acetyl)-1-(2-(tBoc-aminopropyl)) glycine, 17

1,3-Diaminopropane (0.05 mmol) was dissolved in THF (100 mL) and chloroacetic acid (0.045 mmol) was added and the reaction heated at reflux for 4 hours and cooled to room temperature. The solution was diluted with diethyl ether (500 mL) and extracted 3 times with 1N NaOH solution. The combined water layers were acidified to pH=4 and extracted with dichloromethane (5×50 mL). The organic layers were combined, dried, filtered and evaporated to an oil. This oil was dissolved in methanol (1000 mL) and dry HCl gas added. The reaction was heated to reflux and maintained there for 8 hours. The reaction was cooled and evaporated to an oil. This oil was dissolved in dioxane/water and p-nitrophenyl-t-butylcarbonate (0.05 mmol) was added and the pH adjusted to 10. The reaction was stirred for 4 hours, then neutralized and extracted 5 times with dichloromethane. The methyl ester was dissolved in 50% DMF in dichloromethane and to this was added dicyclohexylcarbodiimide (DCC, 0.05 mmol) and hydroxbenzotriazole (0.05 mmol), and 2-thyminylacetic acid (0.05 mmol). The reaction was stirred for 18 hours then the DCC was removed by filtration and the residue evaporated to an oil. The oil was purified by column chromatography.

EXAMPLE 14

3-(Boc-amino)-1,2-propanediol, 18

3-Amino-1,2-propanediol (40.00 g, 0.440 mol, 1.0 eqv) was dissolved in water (1000 ml) and cooled to 0° C., and di-tert-butyl dicarbonate (115.0 g, 0.526 mol, 1.2 eqv) was added in one portion. The reaction mixture was heated to room temperature on a water bath with stirring. The pH was maintained at 10.5 with a solution of sodium hydroxide (17.56 g, 0.440 mol, 1.0 eqv) in water (120 ml). When the addition of aqueous sodium hydroxide was completed, the reaction mixture was stirred overnight at room temperature. Subsequently, ethyl acetate (750 ml) was added to the reaction mixture followed by cooling to 0° C. and the pH was adjusted to 2.5 with 4N sulfuric acid with vigorous stirring. The phases were separated. The water phase was washed with additional ethyl acetate (6×350 ml). The volume of the organic phase was reduced to 900 ml by evaporation under reduced pressure and washed with a saturated aqueous solution of potassium hydrogen sulfate diluted to twice its volume (1×1000 ml) and with saturated aqueous sodium chloride (1×500 ml). The organic phase was dried (MgSO$_4$) and evaporated under reduced pressure to yield 50.12 9 (60%) of the title compound. The product could be solidified by evaporation from methylene chloride and subsequent freezing. $^1$H-NMR (CDCl$_3$/TMS): δ=1.43 (s, 9H, Me$_3$C), 3.25 (m, 2H, CH2), 3.57 (m, 2H, CH$_2$), 3.73 (m, 1H, CH). $^{13}$C-NMR (CDCl$_3$/TMS): δ=28.2 (Me$_3$C), 42.6 (CH$_2$), 63.5, 71.1 (CH$_2$OH, CHOH), 79.5 (Me$_3$C), 157.0 (C=O).

EXAMPLE 15

Boc-aminoacetaldehyde, 19

3-(Boc-amino)-1,2-propanediol (18, 20.76 g, 0.109 mol, 1 eqv) was suspended in water (150 ml). Potassium m-periodate (24.97 g, 0.109 mol, 1 eqv) was added and the reaction mixture was stirred for 2 h at room temperature under nitrogen. The reaction mixture was filtered and the water phase was extracted with chloroform (6×250 ml). The organic phase was dried (MgSO$_4$) and evaporated to afford crude Boc-aminoacetaldehyde as a golden oil. This oil was kugelrohr distilled at 80° C. and 0.2 mbar to yield 13.19 g (76%) of the title compound as a semicrystalline solid. $^1$HNMR (DMSO-d$_6$/TMS): δ=1.47 (s, 9H, Me$_3$C), 3.81 (d, J=5.6 Hz, 2H, CH$_2$), 7.22 (b, 1H, NH), 9.54 (s, 1H, CHO). $^{13}$C-NMR (DMSO-d$_6$/TMS): δ=28.2 (Me$_3$C), 50.5 (CH$_2$), 78.4 (Me$_3$C), 156.1 (carbamate C=O), 200.6 (CHO). Anal. Calcd. for C$_7$H$_{13}$NO$_3$: C, 52.82; H, 8.23; N, 8.80. Found: C, 52.21; H, 8.15; N, 8.46.

EXAMPLE 16

(Boc-amino)ethylglycine Methyl Ester, 20
A. Reduction With Sodium Cyanoborohydride Boc-aminoacetaldehyde (19, 1.00 g, 6.3 mmol, 1 eqv) was dissolved in methanol (50 ml). Anhydrous sodium acetate (1.03 g, 12.6 mmol, 2 eqv), glycine methyl ester hydrochloride (Aldrich Chemical Co., 0.79 g, 6.3 mmol, 1 eqv) and sodium cyanoborohydride (1.97 g, 31.4 mmol, 5 eqv) were added to the solution in that order. The reaction mixture was stirred for 2 h at room temperature under nitrogen. Water (50 ml) was added to the suspension and the resulting clear solution was evaporated under reduced pressure to remove the methanol. The aqueous phase was extracted with methylene chloride (3×100 ml). The organic phase was washed with a saturated aqueous solution of sodium chloride (1×100 ml), dried (Na$_2$SO$_4$), filtered and then evaporated under reduced pressure affording 1.41 g of crude title compound as a yellow oil. The crude product was kugelrohr distilled at 110° C. and 0.5 mbar to yield 0.49 g (34%) of 2-(Boc-amino)ethylglycine methyl ester as a colorless liquid. $^1$H-NMR (CDCl$_3$/TMS) : δ=1.36 (s, 9H, Me$_3$C), 1.91 (s, 1H, NH), 2.67 (t, J=6 Hz, 2H, NHCH$_2$), 3.13 (q, J=6 Hz, 2H, NHCH$_2$), 3.34 (s, 2H, CH$_2$COO), 3.65 (s, 3H, OMe), 5.13 (b, 1H, carbamate NH). $^{13}$C-NMR (CDCl$_3$/TMS): δ=28.2 (Me$_3$C), 39.9, 48.5 (NHCH$_2$), 50.0 (CH$_2$COO), 51.5 (OMe), 78.9 (Me$_3$C), 155.9 (carbamate C=O), 172.6 (ester C=O). Anal. Calcd for C$_{10}$H$_2$N$_2$O$_4$: C, 51.71; H, 8.68; N, 12.06. Found: C, 51.55; H, 8.72; N, 11.79.
B. Catalytic hydrogenation Boc-aminoacetaldehyde (2.08 g, 13.1 mmol, 1 eqv) was dissolved in methanol (50 ml) and cooled to 0° C. Palladium on activated carbon (10%, 0.4 g) was added under nitrogen and with vigorous stirring. Anhydrous sodium acetate (2.14 g, 26.1 mmol, 2 eqv) and glycine methyl ester, hydrochloride (1.64 g, 13.1 mmol, 1 eqv) each dissolved in methanol (25 ml) were added to the mixture. The reaction mixture was hydrogenated at atmospheric pressure and room temperature with vigorous stirring, until hydrogen uptake had ceased (when 287 ml, 13.1 mmol, 1 eqv had been consumed) after about 1 h. The reaction mixture was filtered and the solvent removed under reduced pressure. The residue was suspended in water (30 ml), and during vigorous stirring pH was adjusted to 8 by dropwise addition of 0.5N NaOH. The water phase was extracted with methylene chloride (4×50 ml). The organic phase was dried (Na$_2$SO$_4$), filtered and evaporated under reduced pressure to yield 3.03 g of crude title compound as a golden oil. The crude product was kugelrohr distilled at 100° C and 0.2 mbar to afford 2.33 g (77%) of 2-(Boc-amino)ethylglycine methyl ester as a colorless liquid. The analytical data were in accord with those provided above for the reduction with sodium cyanoborohydride.

EXAMPLE 17

General Method for the Synthesis of PNA Oligomers

Oligomers were prepared generally in accordance with the methods disclosed by WO 92/20702. Benzyhydrylamine resin (initially loaded 0.28 mmol/gm with Boc-L-Lys (2-chlorobenyloxycarbonyl)) was swollen in DMF and an excess of a monomer to be coupled was added, followed by dicyclohexyl-carbodiimide (0.15M in 50% DMF in dichloromethane). The Boc deprotection was accomplished by trifluoroacetic acid treatment. The progress of the coupling reactions was monitored by quantitative ninhydrin analysis. The PNA was released from the resin using anhydrous HF under standard conditions. The products were purified using HPLC with acetonitrile-water (0.1%TFA) gradient and structure confirmed by fast atom bombardment mass spectrometry. The following sequences have been synthesized by this method:

H-T$_{10}$LysNH$_2$ (SEQ ID NO: 1)
H-T$_4$CT$_5$LysNH$_2$ (SEQ ID NO: 2)
H-T$_2$CT$_2$CT$_4$LysNH$_2$ (SEQ ID NO: 3)
H-T$_4$CT$_2$CT$_2$LysNH$_2$ (SEQ ID NO: 4)
H-TGTACGTCACAACTA-NH$_2$ (SEQ ID NO: 5)
H-CCTTCCCTT-NH$_2$ (SEQ ID NO: 6)
H-TTCCCTTCC-NH$_2$ (SEQ ID NO: 7)
H-TAGTTATCTCTATCT-NH$_2$ (SEQ ID NO: 8)
H-TGTACGTCACAACTA-NH$_2$ (SEQ ID NO: 9)
H-GCACAGCC-LYS-NH$_2$ (SEQ ID NO: 10)
H-TTTTCTTTT-NH$_2$ (SEQ ID NO: 110
H-TTTTTTTTTCCCCCCC-NH$_2$ (SEQ ID NO: 12)
H-CCCCCCCTTTTTTTTT-NH$_2$ (SEQ ID NO: 13)
H-CCTCCTTCCC-NH$_2$ (SEQ ID NO: 14)
H-TTCTCTCTCT-NH$_2$ (SEQ ID NO: 15)
H-TTTTTCTCTCTCTCT-NH$_2$ (SEQ ID NO: 16)
H-CCCCCACCACTTCCCCTCTC-(Lys)$_9$NH$_2$ (SEQ ID NO: 17)
H-CTTATATTCCGTCATCGCTCLys-NH$_2$ (SEQ ID NO: 18)
H-CTGTCTCCATCCTCTTCACT-NH$_2$ (SEQ ID NO: 19)
H-TATTCCGTCATCGCTCCTCALys-NH$_2$ (SEQ ID NO: 20)
H-CCCCCACCACTTCCCCTCTC-NH$_2$ (SEQ ID NO: 21)
H-CTGCTGCCTCTGTCTCAGGTLysNH$_2$ (SEQ ID NO: 22)
H-T$_4$-(β-alanine) C-T$_5$LysNH$_2$ (SEQ ID NO: 23)
H-T$_4$-(β-alanine) T-T$_5$LysNH$_2$ (SEQ ID NO: 24)

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having the formula:

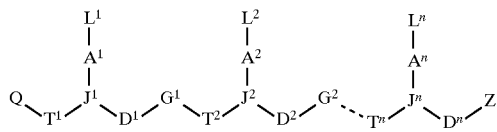

wherein:

n is at least 2, each of $L^1-L^n$ is independently selected from the group consisting of hydrogen, hydroxy, $(C_1-C_4)$alkanoyl, naturally occurring nucleobases, non-naturally occurring nucleobases, aromatic moieties, DNA intercalators, nucleobase-binding groups, heterocyclic moieties, and reporter ligands, at least one of $L^1-L^n$ being a naturally occurring nucleobase, a non-naturally occurring nucleobase, a DNA intercalator, or a nucleobase-binding group;

each of $T^1-T^n$ is $(CR^6R^7)y$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$ or $R^6$ and $R^7$ taken together complete an alicyclic or heterocyclic system;

each $R^3$ and $R^4$ is independently selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino;

$R^5$ is hydrogen, $(C_1-C_6)$alkyl, hydroxy-, alkoxy-, or alkylthio- substituted $(C_1-C_6)$alkyl;

each of $D^1-D^n$ is $(CR^6R^7)_z$ where $R^6$ and $R^7$ are as defined above;

each of y and z is zero or an integer from 1 to 10, the sum y+z being greater than 2 but not more than 10;

each of $G^1-G^{n-1}$ is $-NR^3CO-$ in either orientation, where $R^3$ is as defined above;

each of $A^1-A^n$ and $J^1-J^n$ are selected such that:

(a) A is a group of formula (IIa), (IIb) or (IIc), and J is N or $R^3N^+$, provided that at least one A is a group of formula (IIc) wherein S is an interger from 1 to 5; or (b) A is a group of formula (IId) and J is CH; or (c) A is a group of formula (IIa) or (IIb) and J is N or $R^3N^+$, provided at least one of y or z is not 1 or 2;

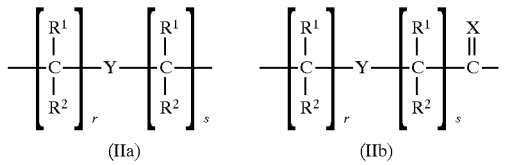

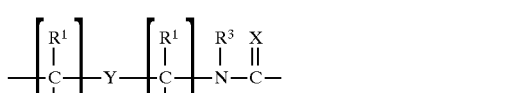

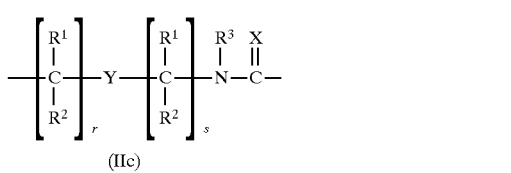

wherein:

X is O, S, Se, $NR^3$, $CH_2$ or $C(CH_3)_2$ where $R^3$ is as defined above;

Y is a single bond, O, S or $NR^4$ where $R^4$ is as defined above;

each of r and s is zero or an integer from 1 to 5;

each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen;

Q is $-CO_2H$, $-CONR^8R^9$, $-SO_3H$ or $-SO_2NR^8R^9$ or an activated derivative of $-CO_2H$ or $-SO_3H$; and Z is $-NHR^{10}R^{11}$ or $-NR^{10}C(O)R^{11}$, where $R^8$, $R^9$, $R^{10}$ and $R^{11}$ are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers.

2. A pharmaceutical composition comprising a compound according to claim 1 and at least one pharmaceutically effective carrier, binder, thickener, diluent, buffer, preservative, or surface active agent.

3. A process for preparing a compound according to claim 28, comprising the steps of:

A) providing a polymer substrate, said polymer being functionalized with a chemical group capable of forming an anchoring linkage with an amino acid;

B) coupling said polymer with a first amino acid through said anchoring linkage, said first amino acid having formula (IV):

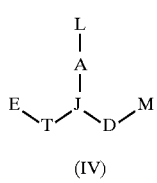

wherein:

L is selected from the group consisting of naturally occurring nucleobases, non-naturally occurring nucleobases, aromatic moieties, DNA intercalators, nucleobase-binding groups, heterocyclic moieties, and reporter ligands, wherein amino groups are, optionally, protected by amino protecting groups;

each T is $(CR^6R^7)y$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$ or $R^6$ and $R^7$ taken together complete an alicyclic or heterocyclic system;

each $R^3$ and $R^4$ is independently selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino;

$R^5$ is hydrogen, $(C_1-C_6)$alkyl, hydroxy-, alkoxy-, or alkylthio-substituted $(C_1-C_6)$alkyl;

each D is $(CR^6R^7)_z$ where $R^6$ and $R^7$ are as defined above;

each of y and z is zero or an integer from 1 to 10, the sum y+z being greater than 2 but not more than 10;

A and J are selected such that:
(a) A is a group of formula (IIc) and J is N or $R^3N^+$; or
(b) A is a group of formula (IId) and J is CH; or
(c) A is a group of formula (IIa) or (IIb) and J is N or $R^3N^+$, provided at least one of y or z is not 1 or 2;

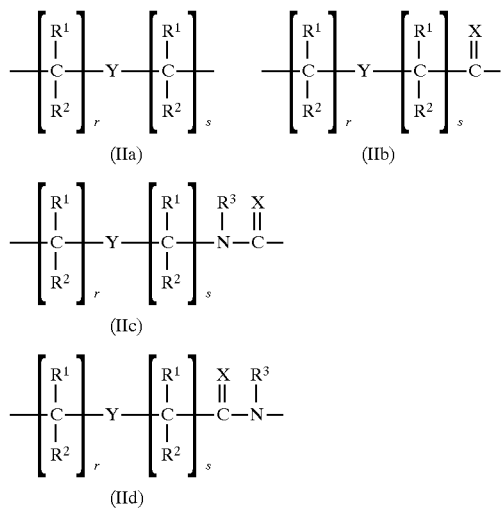

wherein:
X is O, S, Se, $NR^3$, $CH_2$ or $C(CH_3)_2$ where $R^3$ is as defined above;

Y is a single bond, O, S or $NR^4$ where $R^4$ is as defined above;

each of r and s is zero or an integer from 1 to 5;

each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and each E is COOH or an activated or protected derivative thereof; and each M is $NHR^3$ or $NR^3R_{12}$, where $R^3$ is as defined above, and $R^{12}$ is an amino protecting group;

C) removing said amino protecting group from said coupled first amino acid to generate a free amino group; and D) reacting said free amino group with a second amino acid having formula (IV) to form a peptide chain.

4. The process of claim 3 further comprising the steps of:
E) removing said amino protecting group from said second amino acid to generate a terminal free amino group on said peptide chain; and
F) reacting said free amino group on said peptide chain with a further amino acid having formula (IV) to lengthen said peptide chain.

5. The process of claim 4 wherein steps E and F are performed a plurality of times.

6. The process of claim 3 further comprising removing at least one protecting group remaining on the amino acid moieties of the peptide chain.

7. The process of claim 3 further comprising cleaving said anchoring linkage without substantially degrading said peptide chain.

8. The process of claim 3 wherein the polymer substrate contains polystyrene, polyacrylamide, silica, a composite material, cotton, or a derivative thereof.

9. The process of claim 4 wherein the chemical group capable of forming said anchoring linkage is chloro-, bromo- and iodo-substituted alkyl, amino-substituted alkyl, amino and aryl-substituted alkyl, amino- and alkylaryl-substituted alkyl, hydroxy-substituted alkyl, or a derivative thereof having a spacer group that can be cleaved substantially without degradation of said polypeptide.

10. The process of claim 9 wherein chloro-substituted alkyl is chloromethyl, amino-substituted alkyl is aminomethyl, amino- and alkyl-substituted aryl is α-aminobenzyl, amino- and alkylaryl-substituted alkyl is selected from the group consisting of a-amino-3- and α-amino-4-methylbenzyl, and hydroxy-substituted alkyl is hydroxymethyl.

11. The process of claim 9 wherein:
the chemical group is derived from an amino-containing moiety selected from amino-substituted alkyl, amino- and aryl substituted alkyl, and amino- and alkylaryl-substituted alkyl; and
the chemical group includes a spacer group derived from the group consisting of 4-(haloalkyl)aryl-lower alkanoic acids, Boc-aminoacyl-4-(oxymethyl)aryl-lower alkanoic acids, N-Boc-p-acylbenzhydrylamines, N-Boc-4'-(lower alkyl)-p-acylbenzhydrylamines, N-Boc-4'-(lower alkoxy)-p-acylbenzhydrylamines, and 4-hydroxymethylphenoxy-lower alkanoic acids.

* * * * *

UNITED STATES PATENT AND TRADEMARK OFFICE
CERTIFICATE OF CORRECTION

PATENT NO. : 5,773,571
DATED : June 30, 1998
INVENTOR(S) : Peter E. Nielsen, et al.

It is certified that error appears in the above-identified patent and that said Letters Patent is hereby corrected as shown below:

Col. 1, line 8, please delete "(now abandoned)." and insert

-- The entire contents of Application Serial Number 08/108,591 is incorporated herein by reference.--

Col. 8, line 54 please delete "block" and insert --blocks--.

Col. 14, line 43 please delete the number "0" and insert --)--.

Col. 92, line 33 please delete [28] and insert --1--.

Signed and Sealed this

Seventh Day of September, 1999

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,773,571
DATED : June 30, 1998
INVENTOR(S) : Nielsen, et al

It is certified that error appears in the above-indentified patent and that said Letters Patent is hereby corrected as shown below:

Col. 91, line 38, please delete "$(CR^6R^7),$" and insert --$(CR^6R^7)_z$--

Col. 91, line 48, please delete "S" and substitute therefor -- s --.

Signed and Sealed this

Twenty-fourth Day of October, 2000

Attest:

Q. TODD DICKINSON

*Attesting Officer*  *Director of Patents and Trademarks*